(12) United States Patent
Beaurain et al.

(10) Patent No.: US 9,333,095 B2
(45) Date of Patent: May 10, 2016

(54) INTERVERTEBRAL DISC PROSTHESIS, SURGICAL METHODS, AND FITTING TOOLS

(75) Inventors: Jacques Beaurain, Saulon la Chapelle (FR); Joël Delecrin, Vertou (FR); Michel Onimus, Vertou (FR); Hervé Chataignier, Boussieres (FR); Jérôme Allain, Paris (FR); Jean-Paul Frédéric Steib, Strasbourg (FR)

(73) Assignee: LDR Medical, Rosieres Pres Troyes (FR)

( * ) Notice: Subject to any disclaimer, the term of this patent is extended or adjusted under 35 U.S.C. 154(b) by 1025 days.

(21) Appl. No.: 12/025,677

(22) Filed: Feb. 4, 2008

(65) Prior Publication Data
US 2008/0234686 A1   Sep. 25, 2008

Related U.S. Application Data

(63) Continuation of application No. 10/476,565, filed as application No. PCT/IB02/02998 on May 3, 2002, now Pat. No. 7,326,250.

(30) Foreign Application Priority Data

May 4, 2001 (FR) ...................................... 01 05982

(51) Int. Cl.
*A61F 2/44* (2006.01)
*A61F 2/46* (2006.01)
(Continued)

(52) U.S. Cl.
CPC ............. *A61F 2/4611* (2013.01); *A61F 2/4425* (2013.01); *A61B 17/1757* (2013.01);
(Continued)

(58) Field of Classification Search
CPC .................................................... A61B 17/1757
USPC ................. 623/17.11–17.16; 606/99, 96, 104
See application file for complete search history.

(56) References Cited

U.S. PATENT DOCUMENTS

| 566,360 A | 8/1896 | White |
|---|---|---|
| 1,436,573 A | 11/1922 | Choppinet et al. |

(Continued)

FOREIGN PATENT DOCUMENTS

| CA | 2472708 | 2/2005 |
|---|---|---|
| CA | 2533473 | 3/2011 |

(Continued)

OTHER PUBLICATIONS

USPTO OA of Feb. 6, 2007 in U.S. Appl. No. 11/109,276.
(Continued)

*Primary Examiner* — Andrew Yang
(74) *Attorney, Agent, or Firm* — Lauff Law PLLC

(57) ABSTRACT

An intervertebral disc prosthesis designed to be substituted for fibrocartilaginous discs ensures a connection between the vertebra of the vertebra column or the end of the latter. The prosthesis includes a pair of plates spaced from each other by a nucleus. The prosthesis has increased stability by providing the nucleus with a translation or rotation stop, or by inducing an angular correction between its plates contacting vertebra, or a combination of these characteristics. The stop includes parts external to the nucleus and contact surfaces perpendicular to their contact directions. Surgical methods and instrumentation for implanting the prosthesis are also described.

11 Claims, 10 Drawing Sheets

(51) Int. Cl.
   *A61B 17/17*   (2006.01)
   *A61B 17/02*   (2006.01)
   *A61F 2/30*    (2006.01)

(52) U.S. Cl.
   CPC .............. *A61B2017/0256* (2013.01); *A61F 2002/30112* (2013.01); *A61F 2002/30113* (2013.01); *A61F 2002/30125* (2013.01); *A61F 2002/30354* (2013.01); *A61F 2002/30369* (2013.01); *A61F 2002/30372* (2013.01); *A61F 2002/30398* (2013.01); *A61F 2002/30604* (2013.01); *A61F 2002/30642* (2013.01); *A61F 2002/30649* (2013.01); *A61F 2002/30662* (2013.01); *A61F 2002/30663* (2013.01); *A61F 2002/30841* (2013.01); *A61F 2002/30878* (2013.01); *A61F 2002/30884* (2013.01); *A61F 2002/443* (2013.01); *A61F 2002/4627* (2013.01); *A61F 2002/4635* (2013.01); *A61F 2002/4687* (2013.01); *A61F 2220/0025* (2013.01); *A61F 2220/0033* (2013.01); *A61F 2230/0004* (2013.01); *A61F 2230/0006* (2013.01); *A61F 2230/0008* (2013.01); *A61F 2310/00029* (2013.01)

(56) References Cited

U.S. PATENT DOCUMENTS

| | | | |
|---|---|---|---|
| 2,836,442 A | 5/1958 | Moskovitz |
| 3,325,197 A | 6/1967 | Wehner |
| 3,374,786 A | 3/1968 | Callender et al. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-Janz et al. |
| 4,759,769 A | 7/1988 | Hedman et al. |
| 4,787,378 A | 11/1988 | Sodhi |
| 4,787,908 A | 11/1988 | Wyss et al. |
| 4,791,918 A | 12/1988 | Von Hasselbach |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,911,718 A | 3/1990 | Lee et al. |
| 4,932,975 A | 6/1990 | Main et al. |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,242,448 A | 9/1993 | Pettine et al. |
| 5,246,458 A | 9/1993 | Graham |
| 5,258,031 A | 11/1993 | Salib et al. |
| 5,290,312 A | 3/1994 | Kojimoto et al. |
| 5,300,074 A | 4/1994 | Frigg |
| 5,306,309 A | 4/1994 | Wagner et al. |
| 5,314,477 A | 5/1994 | Marnay |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buettner-Janz et al. |
| 5,417,692 A | 5/1995 | Goble et al. |
| 5,417,712 A | 5/1995 | Whittaker et al. |
| 5,425,773 A | 6/1995 | Boyd et al. |
| 5,429,641 A | 7/1995 | Gotfried |
| 5,437,674 A | 8/1995 | Worcel et al. |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,507,816 A | 4/1996 | Bullivant |
| 5,522,845 A | 6/1996 | Wenstrom, Jr. |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buettner-Janz et al. |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,636 A | 3/1997 | Kohrs et al. |
| 5,613,974 A | 3/1997 | Andreas et al. |

(56) References Cited

U.S. PATENT DOCUMENTS

| | | | |
|---|---|---|---|
| 5,620,012 | A | 4/1997 | Benderev et al. |
| 5,643,321 | A | 7/1997 | McDevitt |
| 5,645,596 | A | 7/1997 | Kim |
| 5,674,294 | A | 10/1997 | Bainville et al. |
| 5,676,701 | A | 10/1997 | Yuan et al. |
| 5,676,702 | A | 10/1997 | Ratron |
| 5,683,465 | A | 11/1997 | Shinn et al. |
| 5,702,449 | A | 12/1997 | McKay |
| 5,702,450 | A | 12/1997 | Bisserie |
| 5,702,472 | A | 12/1997 | Huebner |
| 5,722,977 | A | 3/1998 | Wilhelmy |
| 5,741,253 | A | 4/1998 | Michelson |
| 5,766,252 | A | 6/1998 | Henry et al. |
| 5,766,253 | A | 6/1998 | Brosnahan, III |
| 5,772,661 | A | 6/1998 | Michelson |
| 5,776,199 | A | 7/1998 | Michelson |
| 5,782,832 | A | 7/1998 | Larsen et al. |
| 5,782,919 | A | 7/1998 | Zdeblick et al. |
| 5,797,909 | A | 8/1998 | Michelson |
| 5,800,550 | A | 9/1998 | Sertich |
| 5,824,094 | A | 10/1998 | Serhan et al. |
| 5,827,328 | A | 10/1998 | Buttermann |
| 5,865,848 | A | 2/1999 | Baker |
| 5,888,224 | A | 3/1999 | Beckers et al. |
| 5,888,226 | A | 3/1999 | Rogozinski |
| 5,893,889 | A | 4/1999 | Harrington |
| 5,895,427 | A | 4/1999 | Kuslich et al. |
| 5,895,428 | A | 4/1999 | Berry |
| 5,899,941 | A | 5/1999 | Nishijima et al. |
| 5,968,098 | A | 10/1999 | Winslow |
| 5,980,522 | A | 11/1999 | Koros et al. |
| 5,984,967 | A | 11/1999 | Zdeblick et al. |
| 6,001,130 | A | 12/1999 | Bryan et al. |
| 6,010,502 | A | 1/2000 | Bagby |
| 6,033,438 | A | 3/2000 | Bianchi et al. |
| 6,039,763 | A | 3/2000 | Shelokov |
| 6,045,552 | A | 4/2000 | Zucherman et al. |
| 6,063,088 | A | 5/2000 | Winslow |
| 6,063,121 | A | 5/2000 | Xavier et al. |
| 6,080,158 | A | 6/2000 | Lin |
| 6,093,205 | A | 7/2000 | McLeod et al. |
| 6,096,038 | A | 8/2000 | Michelson |
| 6,096,080 | A | 8/2000 | Nicholson et al. |
| 6,099,531 | A | 8/2000 | Bonutti |
| 6,102,950 | A | 8/2000 | Vaccaro |
| 6,113,637 | A | 9/2000 | Gill et al. |
| 6,113,638 | A | 9/2000 | Williams et al. |
| 6,129,763 | A | 10/2000 | Chauvin et al. |
| 6,136,031 | A | 10/2000 | Middleton |
| 6,146,421 | A | 11/2000 | Gordon et al. |
| 6,146,422 | A | 11/2000 | Lawson |
| 6,149,650 | A | 11/2000 | Michelson |
| 6,156,067 | A | 12/2000 | Bryan et al. |
| 6,179,873 | B1 | 1/2001 | Zientek |
| 6,179,874 | B1 | 1/2001 | Cauthen |
| 6,193,757 | B1 | 2/2001 | Foley et al. |
| 6,206,922 | B1 | 3/2001 | Zdeblick et al. |
| 6,210,412 | B1 | 4/2001 | Michelson |
| 6,214,050 | B1 | 4/2001 | Huene |
| 6,221,077 | B1 | 4/2001 | Rinner et al. |
| 6,224,595 | B1 | 5/2001 | Michelson |
| 6,224,607 | B1 | 5/2001 | Michelson |
| 6,228,118 | B1 | 5/2001 | Gordon |
| 6,231,609 | B1 | 5/2001 | Mehdizadeh |
| 6,241,769 | B1 | 6/2001 | Nicholson et al. |
| 6,245,072 | B1 | 6/2001 | Zdeblick et al. |
| 6,258,094 | B1 | 7/2001 | Nicholson et al. |
| 6,261,293 | B1 | 7/2001 | Nicholson et al. |
| 6,264,656 | B1 | 7/2001 | Michelson |
| 6,267,763 | B1 | 7/2001 | Castro |
| 6,270,498 | B1 | 8/2001 | Michelson |
| 6,277,149 | B1 | 8/2001 | Boyle et al. |
| 6,283,998 | B1 | 9/2001 | Eaton |
| 6,296,664 | B1 | 10/2001 | Middleton |
| 6,302,914 | B1 | 10/2001 | Michelson |
| 6,306,170 | B2 | 10/2001 | Ray |
| 6,315,797 | B1 | 11/2001 | Middleton |
| 6,319,257 | B1 | 11/2001 | Carignan et al. |
| 6,344,057 | B1 | 2/2002 | Rabbe et al. |
| 6,364,880 | B1 | 4/2002 | Michelson |
| 6,368,350 | B1 | 4/2002 | Erickson et al. |
| 6,371,988 | B1 | 4/2002 | Pafford et al. |
| 6,375,655 | B1 | 4/2002 | Zdeblick et al. |
| 6,387,130 | B1 | 5/2002 | Stone et al. |
| 6,395,035 | B2 | 5/2002 | Bresina et al. |
| 6,402,750 | B1 | 6/2002 | Atkinson et al. |
| 6,402,785 | B1 | 6/2002 | Zdeblick et al. |
| 6,409,765 | B1 | 6/2002 | Bianchi et al. |
| 6,413,278 | B1 | 7/2002 | Marchosky |
| 6,416,551 | B1 | 7/2002 | Keller |
| 6,419,703 | B1 | 7/2002 | Fallin et al. |
| 6,419,704 | B1 | 7/2002 | Ferree |
| 6,419,706 | B1 | 7/2002 | Graf |
| 6,423,063 | B1 | 7/2002 | Bonutti |
| 6,423,095 | B1 | 7/2002 | Van Hoeck et al. |
| 6,440,168 | B1 | 8/2002 | Cauthen |
| 6,447,512 | B1 | 9/2002 | Landry et al. |
| 6,447,544 | B1 | 9/2002 | Michelson |
| 6,447,546 | B1 | 9/2002 | Bramlet et al. |
| 6,447,547 | B1 | 9/2002 | Michelson |
| 6,468,310 | B1 | 10/2002 | Ralph et al. |
| 6,471,724 | B2 | 10/2002 | Zdeblick et al. |
| 6,478,800 | B1 | 11/2002 | Fraser et al. |
| 6,478,823 | B1 | 11/2002 | Michelson |
| 6,482,234 | B1 | 11/2002 | Weber et al. |
| 6,485,517 | B1 | 11/2002 | Michelson |
| 6,500,205 | B1 | 12/2002 | Michelson |
| 6,506,216 | B1 | 1/2003 | McCue et al. |
| 6,514,260 | B1 | 2/2003 | Zdeblick et al. |
| 6,517,580 | B1 | 2/2003 | Ramadan et al. |
| 6,520,967 | B1 | 2/2003 | Cauthen |
| 6,520,996 | B1 | 2/2003 | Manasas et al. |
| 6,524,312 | B2 | 2/2003 | Landry et al. |
| 6,527,804 | B1 | 3/2003 | Gauchet et al. |
| 6,527,806 | B2 | 3/2003 | Ralph et al. |
| 6,540,785 | B1 | 4/2003 | Gill et al. |
| 6,558,423 | B1 | 5/2003 | Michelson |
| 6,565,605 | B2 | 5/2003 | Goble et al. |
| 6,572,653 | B1 | 6/2003 | Simonson |
| 6,579,291 | B1 | 6/2003 | Keith et al. |
| 6,579,320 | B1 | 6/2003 | Gauchet et al. |
| 6,582,468 | B1 | 6/2003 | Gauchet |
| 6,592,624 | B1 | 7/2003 | Fraser et al. |
| 6,599,294 | B2 * | 7/2003 | Fuss et al. .................. 606/99 |
| 6,599,320 | B1 | 7/2003 | Kuslich et al. |
| 6,607,530 | B1 | 8/2003 | Carl et al. |
| 6,607,558 | B2 | 8/2003 | Kuras |
| 6,610,089 | B1 | 8/2003 | Liu et al. |
| 6,610,092 | B2 | 8/2003 | Ralph et al. |
| 6,610,093 | B1 | 8/2003 | Pisharodi |
| 6,613,091 | B1 | 9/2003 | Zdeblick et al. |
| 6,616,671 | B2 | 9/2003 | Landry et al. |
| 6,641,614 | B2 | 11/2003 | Wagner et al. |
| 6,645,206 | B1 | 11/2003 | Zdeblick et al. |
| 6,645,249 | B2 | 11/2003 | Ralph et al. |
| 6,648,893 | B2 | 11/2003 | Dudasik |
| 6,652,533 | B2 | 11/2003 | O'Neil |
| 6,652,586 | B2 | 11/2003 | Hunter et al. |
| 6,656,224 | B2 | 12/2003 | Middleton |
| 6,669,730 | B2 | 12/2003 | Ralph et al. |
| 6,669,731 | B2 | 12/2003 | Ralph et al. |
| 6,669,732 | B2 | 12/2003 | Serhan et al. |
| 6,673,113 | B2 | 1/2004 | Ralph et al. |
| 6,679,887 | B2 | 1/2004 | Nicholson et al. |
| 6,679,915 | B1 | 1/2004 | Cauthen |
| 6,682,562 | B2 | 1/2004 | Viart et al. |
| 6,695,851 | B2 | 2/2004 | Zdeblick et al. |
| 6,695,882 | B2 | 2/2004 | Bianchi et al. |
| 6,706,068 | B2 | 3/2004 | Ferree |
| 6,709,439 | B2 | 3/2004 | Rogers et al. |
| 6,709,458 | B2 | 3/2004 | Michelson |
| 6,716,247 | B2 | 4/2004 | Michelson |
| 6,719,794 | B2 | 4/2004 | Gerber et al. |
| 6,723,127 | B2 | 4/2004 | Ralph et al. |

(56) References Cited

U.S. PATENT DOCUMENTS

| | | | |
|---|---|---|---|
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,749,636 B2 | 6/2004 | Michelson |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,678 B2 | 9/2004 | Hawkins |
| 6,793,679 B2 | 9/2004 | Michelson |
| 6,800,093 B2 | 10/2004 | Nicholson et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |
| 6,962,606 B2 | 11/2005 | Michelson |
| 6,964,686 B2 | 11/2005 | Gordon |
| 6,966,929 B2 | 11/2005 | Mitchell |
| 6,972,019 B2 | 12/2005 | Michelson |
| 6,972,035 B2 | 12/2005 | Michelson |
| 6,981,975 B2 | 1/2006 | Michelson |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,385 B2 | 2/2006 | Bonutti |
| 7,001,432 B2 | 2/2006 | Keller et al. |
| 7,008,453 B1 | 3/2006 | Michelson |
| 7,011,684 B2 | 3/2006 | Eckman |
| 7,025,787 B2 | 4/2006 | Bryan et al. |
| 7,033,394 B2 | 4/2006 | Michelson |
| 7,041,135 B2 | 5/2006 | Michelson |
| 7,041,136 B2 | 5/2006 | Goble et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,105,023 B2 | 9/2006 | Eckman |
| 7,105,024 B2 | 9/2006 | Richelsoph |
| 7,112,206 B2 | 9/2006 | Michelson |
| 7,118,579 B2 | 10/2006 | Michelson |
| 7,118,580 B1 | 10/2006 | Byersdorff et al. |
| 7,118,598 B2 | 10/2006 | Michelson |
| 7,128,760 B2 | 10/2006 | Michelson |
| 7,128,761 B2 | 10/2006 | Kuras et al. |
| 7,153,325 B2 | 12/2006 | Kim et al. |
| 7,163,561 B2 | 1/2007 | Michelson |
| 7,169,153 B2 | 1/2007 | Keller |
| 7,175,662 B2 | 2/2007 | Link et al. |
| 7,179,294 B2 | 2/2007 | Eisermann et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,292 B2 | 5/2007 | Ralph et al. |
| 7,217,293 B2 | 5/2007 | Branch, Jr. |
| 7,223,289 B2 | 5/2007 | Trieu et al. |
| 7,232,463 B2 | 6/2007 | Falahee |
| 7,232,464 B2 | 6/2007 | Mathieu et al. |
| 7,291,170 B2 | 11/2007 | Huppert |
| 7,326,248 B2 | 2/2008 | Michelson |
| 7,326,250 B2 | 2/2008 | Beaurain et al. |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,692 B2 | 11/2008 | Michelson |
| 7,465,317 B2 | 12/2008 | Malberg et al. |
| 7,494,508 B2 | 2/2009 | Zeegers |
| 7,503,933 B2 | 3/2009 | Michelson |
| 7,540,882 B2 | 6/2009 | Michelson |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,632,282 B2 | 12/2009 | Dinville |
| 7,637,951 B2 | 12/2009 | Michelson |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,727,280 B2 | 6/2010 | McLuen |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |

(56) References Cited

U.S. PATENT DOCUMENTS

| | | |
|---|---|---|
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 2001/0020185 A1 | 9/2001 | Ray |
| 2002/0040243 A1 | 4/2002 | Attali et al. |
| 2002/0087212 A1 | 7/2002 | James et al. |
| 2002/0143343 A1 | 10/2002 | Castro |
| 2002/0161444 A1 | 10/2002 | Choi |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0055503 A1 | 3/2003 | O'Neil |
| 2003/0069586 A1 | 4/2003 | Errico et al. |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0109928 A1 | 6/2003 | Pasquet et al. |
| 2003/0135279 A1 | 7/2003 | Michelson |
| 2003/0149438 A1 | 8/2003 | Nichols et al. |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0102846 A1 | 5/2004 | Keller et al. |
| 2004/0111160 A1 | 6/2004 | Evans et al. |
| 2004/0117022 A1 | 6/2004 | Marnay et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0210313 A1 | 10/2004 | Michelson |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz |
| 2005/0038512 A1 | 2/2005 | Michelson |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | McDonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Millard |
| 2006/0058878 A1 | 3/2006 | Michelson |
| 2006/0069437 A1 | 3/2006 | Weber |
| 2006/0069441 A1 | 3/2006 | Zucherman et al. |
| 2006/0085076 A1 | 4/2006 | Krishna et al. |

(56) References Cited

U.S. PATENT DOCUMENTS

| | | |
|---|---|---|
| 2006/0085077 A1 | 4/2006 | Cook et al. |
| 2006/0095136 A1 | 5/2006 | McLuen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | McLuen |
| 2006/0259143 A1 | 11/2006 | Navarro et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1 | 4/2007 | Bonutti et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1 | 7/2007 | Rashbaum et al. |
| 2007/0250167 A1 | 10/2007 | Bray et al. |
| 2007/0250168 A1 | 10/2007 | Lechmann et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0295371 A1 | 12/2011 | Moskowitz et al. |
| 2011/0301713 A1 | 12/2011 | Theofilos |

(56) References Cited

U.S. PATENT DOCUMENTS

| | | |
|---|---|---|
| 2011/0301714 A1 | 12/2011 | Theofilos |
| 2011/0313528 A1 | 12/2011 | Laubert et al. |
| 2012/0053693 A1 | 3/2012 | Zeegers |

FOREIGN PATENT DOCUMENTS

| | | |
|---|---|---|
| DE | 2263842 A | 7/1974 |
| DE | 2804936 | 8/1979 |
| DE | 3023353 A | 4/1981 |
| DE | 8912648 U | 11/1990 |
| DE | 4328690 | 3/1995 |
| DE | 29911422 | 8/1999 |
| DE | 20310432 U | 9/2003 |
| DE | 20310433 U | 9/2003 |
| DE | 20320454 | 10/2004 |
| DE | 10323363 | 12/2004 |
| DE | 102004027986 | 7/2005 |
| EP | 42271 | 12/1981 |
| EP | 176728 | 4/1986 |
| EP | 0298235 A | 1/1989 |
| EP | 0317972 A | 5/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |
| EP | 0637439 | 2/1995 |
| EP | 0697200 | 2/1996 |
| EP | 0566810 B1 | 5/1996 |
| EP | 0738504 | 10/1996 |
| EP | 0747025 A1 | 12/1996 |
| EP | 0852934 | 7/1998 |
| EP | 0903126 | 3/1999 |
| EP | 0951879 | 10/1999 |
| EP | 0955021 A | 11/1999 |
| EP | 0978258 | 2/2000 |
| EP | 1222903 | 7/2002 |
| EP | 1250898 A1 | 10/2002 |
| EP | 1287795 | 3/2003 |
| EP | 1344506 | 9/2003 |
| EP | 1344508 | 9/2003 |
| EP | 1504733 | 2/2005 |
| EP | 1374808 | 12/2005 |
| FR | 212815 A | 9/1972 |
| FR | 2372622 | 6/1978 |
| FR | 2632516 A | 12/1989 |
| FR | 2659226 A | 9/1991 |
| FR | 2716619 | 9/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 A | 2/1997 |
| FR | 2787019 | 12/1998 |
| FR | 2787021 A | 6/2000 |
| FR | 2824261 | 11/2002 |
| FR | 2831796 | 5/2003 |
| FR | 2843293 | 2/2004 |
| FR | 2846550 | 5/2004 |
| FR | 2865629 | 8/2005 |
| FR | 2865630 A1 | 8/2005 |
| FR | 2869528 | 11/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| JP | 2261446 | 10/1990 |
| WO | WO9011740 | 10/1990 |
| WO | WO9011740 A | 10/1990 |
| WO | WO9107931 | 6/1991 |
| WO | WO9113598 A | 9/1991 |
| WO | WO9301771 A | 2/1993 |
| WO | WO9404100 | 3/1994 |
| WO | WO9515133 | 6/1995 |
| WO | WO9817209 | 4/1998 |
| WO | WO9909914 | 3/1999 |
| WO | WO9953871 | 10/1999 |
| WO | WO9956675 A | 11/1999 |
| WO | WO9956676 | 11/1999 |
| WO | WO9965412 | 12/1999 |
| WO | WO9966864 | 12/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO0141680 | 6/2001 |
| WO | WO0143620 | 6/2001 |
| WO | WO0162191 | 8/2001 |
| WO | WO0213732 | 2/2002 |
| WO | WO02058599 | 8/2002 |
| WO | WO02071960 | 9/2002 |
| WO | WO02089701 A2 | 11/2002 |
| WO | WO03005939 | 1/2003 |
| WO | WO03015646 | 2/2003 |
| WO | WO03026522 | 4/2003 |
| WO | WO03039400 A2 | 5/2003 |
| WO | WO03045262 | 6/2003 |
| WO | WO03059212 A | 7/2003 |
| WO | WO03075803 | 9/2003 |
| WO | WO03075804 A | 9/2003 |
| WO | WO2004034935 | 4/2004 |
| WO | WO2004039291 | 5/2004 |
| WO | WO2004041129 A1 | 5/2004 |
| WO | WO2004041131 | 5/2004 |
| WO | WO2004071360 | 8/2004 |
| WO | WO2004089256 | 10/2004 |
| WO | WO2005007040 | 1/2005 |
| WO | WO2005046534 | 5/2005 |
| WO | WO2005051243 | 6/2005 |
| WO | WO2005074839 | 8/2005 |
| WO | WO2005104395 | 11/2005 |
| WO | WO2005117728 | 12/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2006136760 | 12/2006 |
| WO | WO2007000654 | 1/2007 |
| WO | WO2007034310 | 3/2007 |
| WO | WO2007063398 | 6/2007 |
| WO | WO2007078978 | 7/2007 |
| WO | WO2008099277 | 8/2008 |
| WO | WO2008149223 | 12/2008 |
| WO | WO2009033100 | 3/2009 |
| WO | WO2011080535 | 7/2011 |

OTHER PUBLICATIONS

USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's Response to USPTO OA of Feb. 13, 2009 in U.S. Appl. No. 11/109,276.
USPTO OA of Apr. 18, 2007 in U.S. Appl. No. 10/533,846.
Applicants' Response to USPTO OA of Apr. 18, 2007 in U.S. Appl. No. 10/533,846.
USPTO OA of Dec. 26, 2007 in U.S. Appl. No. 10/533,846.
Applicants' Response to USPTO OA of Dec. 26, 2007 in U.S. Appl. No. 10/533,846.
USPTO OA of Oct. 15, 2008 in U.S. Appl. No. 10/533,846.
Applicants' Response to USPTO OA of Oct. 15, 2008 in U.S. Appl. No. 10/533,846.

(56) References Cited

OTHER PUBLICATIONS

USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Apr. 13, 2009 in U.S. Appl. No. 11/341,007.
USPTO OA of Mar. 20, 2009 in U.S. Appl. No. 11/676,237.
USPTO OA of Feb. 18, 2009 in U.S. Appl. No. 11/632,253.
Applicants' Response to USPTO OA of Feb. 18, 2009 in U.S. Appl. No. 11/632,253.
A biological basis for instantaneous centres of rotation of the vertebral column. N. Bouduk, B. Amevo, M. Pearcy, Proc Insititution Mechanical Engineers, Jun. 16, 1995, pp. 177-183.
A Multicenter Retrospective Study of the Clinical Results of the LINK SB Charite Intervertebral Prosthesis, S. L. Griffith, PhD, A. P. Shelokov, MD, K. Buttner-Janz, MD, Jean-Phillipe LeMaire, MD and W. S. Zeegers, MD, Spine, vol. 19, No. 16, pp. 1842-1849, Mar. 21, 1994.
A New Technique for the Three-Dimensional Study of the Spine in Vitro and In Vivo by Using a Motion-Analysis System, X. Liu, G. Fabry, K. Labey, L. Van Den Berghe, R. Van Audekercke, G. Molenaers, P. Moens. Journal of Spinal Disorders, vol. 10, No. 4, pp. 329-338, Jan. 30, 1997.
Alternatives to Spinal Fusion, J. P. Kostuik, Spinal Fusion, vol. 29, No. 4, Oct. 1998, pp. 701-415.
Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Tile, MD, BSc, (MED), FRCS ©, and B. Cruickshank, MD, FRCPath, Spine, vol. 10., No. 3, pp. 257-261, Jan. 21, 1984.
Clinical Biomechanics of the Spine, A. A. White III, M. M. Panjabi, pp. 128-130, 2nd Edition, J.B. Lippincott Co., 1990.
Computer Analysis of Spinal Segment Motion in Degenerative Disc Disease With and Without Axial Loading, J.V. Seligman, S.D. Gertzbein, M. Tile, A., Kapasouri, Spine, vol. 9., No. 6, pp. 566-573, Dec. 31, 1983.
FR 2 718 635 Preliminary Search Report, National Institute of Industrial Property (France), Jan. 16, 1995.
FR 2 730 159 Preliminary Search Report, National Institute of Industrial Property (France), Sep. 29, 1995.
FR 2 824 261 Preliminary Search Report, National Institute of Industrial Property (France), Feb. 25, 2002.
FR 2 831 796 Prelininary Search Report, National Institute of Industrial Property (France), Aug. 2, 2002.
FR 2 846 550 Prelininary Search Report, National Institute of Industrial Property (France), Jul. 10, 2003.
FR 2 865 629 Prelininary Search Report, National Institute of Industrial Property (France), Sep. 14, 2004.
FR 2 865 630 Prelininary Search Report, National Institute of Industrial Property (France), Jan. 12, 2005.
FR 2 869 528 Prelininary Search Report, National Institute of Industrial Property (France), Dec. 13, 2004.
Instantantaneous Axis of Rotation as a Function of the Three Columns of the Spine, T. R. Haher, MD, M. O'Brien, MD, W. T. Felmly, MD, D. Welin, MD, G. Perrier, MD., J. Choueka, MD, V. Devlin, MD, A. Vassiliou, ME, and G. Chow, MS, Spine, vol. 17, No. 6, pp. S149-S154, Jan. 9, 1992.
Instantantaneous Axis of Rotation of the Lumbar Intervertebral Joints, M. J. Pearcy, H. Bogduk, Spine, vol. 13, No. 9, pp. 1033-1041, Nov. 15, 1987.
Mobidisc (website) 1 page, www.ldrmedical.fr/mobidisc.htm, Sep. 19, 2004.
Motion Characteristics of the Normal Lumbar Spine in Young Adults: Instantaneous of Axis of Rotation and Vertebral Center Motion Analysis, T. Yoshioka, H. Tsuji, N. Hirano and S. Sainoh, Journal of Spinal Disorders, vol. 3, No. 2, pp. 103-113, 1990.
PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.
Relocation of the Bending Axis During Flexion-Extension of Lumbar Intervertebral Discs and its Implications for Prolapse, J.A. Klein and D.W.L. Hukins,Spine, vol. 8, No. 6, pp. 659-664, Nov. 18, 1982.
The Effect of the Three Columns of the Spine on the Instantaneous Axis of Rotation in Flexion and Extension, T. R. Haher, M. Bergman, M. O'Brien, W. T. Felmly, J. Choueka, D. Welin, G. Chow, A. Vassiliou, Spine, vol. 16, No. 8, pp. S312-S318, Apr. 16, 1991.
U.S. Patent & Trademark Office; Notice of Allowance in U.S. Appl. No. 10/494,418; Sep. 20, 2005; USPTO; Alexandria, Virgina; All Pages.
U.S. Patent & Trademark Office; Notice of Allowance in U.S. Appl. No. 10/533,846; Nov. 4, 2009; USPTO; Alexandria, Virgina; All Pages.
LDR Medical, by its attorneys; Reply to Office Action in U.S. Appl. No. 12/424,364; Feb. 27, 2012; USPTO; Alexandria, Virgina; All Pages.
U.S. Patent & Trademark Office; Office Action in U.S. Appl. No. 12/424,364; Jan. 26, 2012; USPTO; Alexandria, Virgina; All Pages.
LDR Medical, by its attorneys; Reply to Office Action in U.S. Appl. No. 12/424,364; Nov. 18, 2011; USPTO; Alexandria, Virgina; All Pages.
U.S. Patent & Trademark Office; Office Action in U.S. Appl. No. 12/424,364; May 18, 2011; USPTO; Alexandria, Virgina; All Pages.
U.S. Patent & Trademark Office; Office Action in U.S. Appl. No. 11/051,710; Dec. 15, 2011; USPTO; Alexandria, Virgina; All Pages.
LDR Medical, by its attorneys; Reply to Office Action in U.S. Appl. No. 11/051,710; Oct. 11, 2011; USPTO; Alexandria, Virgina; All Pages.
U.S. Patent & Trademark Office; Office Action in U.S. Appl. No. 11/051,710; Apr. 11, 2011; USPTO; Alexandria, Virgina; All Pages.
LDR Medical, by its attorneys; Reply to Office Action in U.S. Appl. No. 11/051,710; Jan. 20, 2011; USPTO; Alexandria, Virgina; All Pages.
U.S. Patent & Trademark Office; Office Action in U.S. Appl. No. 11/051,710; Jul. 20, 2010; USPTO; Alexandria, Virgina; All Pages.
LDR Medical, by its attorneys; Reply to Office Action in U.S. Appl. No. 11/051,710; Apr. 26, 2010; USPTO; Alexandria, Virgina; All Pages.
U.S. Patent & Trademark Office; Office Action in U.S. Appl. No. 11/051,710; Oct. 26, 2009; USPTO; Alexandria, Virgina; All Pages.
U.S. Patent & Trademark Office; Notice of Allowance in U.S. Appl. No. 11/098,266; Apr. 21, 2008; USPTO; Alexandria, Virgina; All Pages.
LDR Medical, by its attorneys; Reply to Office Action in U.S. Appl. No. 11/098,266; Feb. 6, 2008; USPTO; Alexandria, Virgina; All Pages.
U.S. Patent & Trademark Office; Office Action in U.S. Appl. No. 11/098,266; Aug. 6, 2007; USPTO; Alexandria, Virgina; All Pages.
LDR Medical, by its attorneys; Reply to Office Action in U.S. Appl. No. 11/098,266; May 23, 2007; USPTO; Alexandria, Virgina; All Pages.
U.S. Patent & Trademark Office; Office Action in U.S. Appl. No. 11/098,266; Nov. 29, 2006; USPTO; Alexandria, Virgina; All Pages.
LDR Medical, by its attorneys; Reply to Office Action in U.S. Appl. No. 11/098,266; Aug. 22, 2006; USPTO; Alexandria, Virgina; All Pages.
U.S. Patent & Trademark Office; Office Action in U.S. Appl. No. 11/098,266; Mar. 22, 2006; USPTO; Alexandria, Virgina; All Pages.
U.S. Patent & Trademark Office; Notice of Allowance in U.S. Appl. No. 12/391,086; Apr. 15, 2011; USPTO; Alexandria, Virgina; All Pages.
LDR Medical, by its attorneys; Reply to Office Action in U.S. Appl. No. 12/391,086; Jan. 31, 2011; USPTO; Alexandria, Virgina; All Pages.

(56) References Cited

OTHER PUBLICATIONS

U.S. Patent & Trademark Office; Office Action in U.S. Appl. No. 12/391,086; Jul. 29, 2010; USPTO; Alexandria, Virgina; All Pages.
U.S. Patent & Trademark Office; Notice of Allowance in U.S. Appl. No. 11/109,276; Dec. 8, 2009; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
LDR Medical, by its attorneys; Reply to Office Action in U.S. Appl. No. 12/360,050; Mar. 6, 2012; USPTO; Alexandria, Virgina; All Pages.
U.S. Patent & Trademark Office; Office Action in U.S. Appl. No. 12/360,050; Sep. 6, 2011; USPTO; Alexandria, Virgina; All Pages.
LDR Medical, by its attorneys; Reply to Office Action in U.S. Appl. No. 12/360,050; Jun. 16, 2011; USPTO; Alexandria, Virgina; All Pages.
U.S. Patent & Trademark Office; Office Action in U.S. Appl. No. 12/360,050; Dec. 17, 2010; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.
U.S. Patent & Trademark Office; Notice of Allowance in U.S. Appl. No. 11/180,868; Jul. 17, 2009; USPTO; Alexandria, Virgina; All Pages.
LDR Medical, by its attorneys; Reply to Office Action in U.S. Appl. No. 12/435,955; Apr. 11, 2012; USPTO; Alexandria, Virgina; All Pages.
U.S. Patent & Trademark Office; Office Action in U.S. Appl. No. 12/435,955; Oct. 11, 2011; USPTO; Alexandria, Virgina; All Pages.
U.S. Patent & Trademark Office; Notice of Allowance in U.S. Appl. No. 11/341,007; Jul. 26, 2010; USPTO; Alexandria, Virgina; All Pages.
LDR Medical, by its attorneys; Reply to Office Action in U.S. Appl. No. 11/341,007; Jun. 17, 2010; USPTO; Alexandria, Virgina; All Pages.
U.S. Patent & Trademark Office; Office Action in U.S. Appl. No. 11/341,007; Dec. 17, 2009; USPTO; Alexandria, Virgina; All Pages.
LDR Medical, by its attorneys; Reply to Office Action in U.S. Appl. No. 11/341,007; Oct. 13, 2009; USPTO; Alexandria, Virgina; All Pages.
LDR Medical, by its attorneys; Reply to Office Action in U.S. Appl. No. 12/955,898; Apr. 19, 2012; USPTO; Alexandria, Virgina; All Pages.
U.S. Patent & Trademark Office; Office Action in U.S. Appl. No. 11/362,253; Mar. 8, 2011; USPTO; Alexandria, Virgina; All Pages.
LDR Medical by its attorneys; Appeal Brief in U.S. Appl. No. 11/362,253; Apr. 9, 2012; USPTO; Alexandria, Virgina; All Pages.
LDR Medical by its attorneys; Reply to Office Action in U.S. Appl. No. 11/362,253; Dec. 20, 2010; USPTO; Alexandria, Virgina; All Pages.
U.S. Patent & Trademark Office; Office Action in U.S. Appl. No. 11/362,253; Jun. 18, 2010; USPTO; Alexandria, Virgina; All Pages.
LDR Medical, by its attorneys; Reply to Office Action in U.S. Appl. No. 11/362,253; Apr. 15, 2010; USPTO; Alexandria, Virgina; All Pages.
U.S. Patent & Trademark Office; Office Action in U.S. Appl. No. 11/362,253; Oct. 15, 2009; USPTO; Alexandria, Virgina; All Pages.
U.S. Patent & Trademark Office; Office Action in U.S. Appl. No. 12/134,884; Jan. 31, 2012; USPTO; Alexandria, Virgina; All Pages.
U.S. Patent & Trademark Office; Office Action in U.S. Appl. No. 11/676,237; Feb. 16, 2012; USPTO; Alexandria, Virgina; All Pages.
LDR Medical, by its attorneys; Appeal Brief in U.S. Appl. No. 11/676,237; Oct. 17, 2011; USPTO; Alexandria, Virgina; All Pages.
U.S. Patent & Trademark Office; Office Action in U.S. Appl. No. 11/676,237; Sep. 15, 2010; USPTO; Alexandria, Virgina; All Pages.
LDR Medical, by its attorneys; Reply to Office Action in U.S. Appl. No. 11/676,237; Jun. 18, 2010; USPTO; Alexandria, Virgina; All Pages.
U.S. Patent & Trademark Office; Office Action in U.S. Appl. No. 11/676,237; Dec. 18, 2009; USPTO; Alexandria, Virgina; All Pages.
LDR Medical, by its attorneys; Reply to Office Action in U.S. Appl. No. 11/676,237; Sep. 21, 2009; USPTO; Alexandria, Virgina; All Pages.
U.S. Patent & Trademark Office; Office Action in U.S. Appl. No. 12/527,373; Dec. 12, 2011; USPTO; Alexandria, Virgina; All Pages.
World Intellectual Property Organization; International Preliminary Report on Patentability for PCT Pub'n No. WO2005074839; Jan. 16, 2006; WIPO; Geneva, Switzerland; all pages.
World Intellectual Property Organization; Written Opinon of the International Searching Authority for PCT Pub'n No. WO2005074839; Jun. 24, 2005; WIPO; Geneva, Switzerland; all pages.
World Intellectual Property Organization; International Preliminary Report on Patentability for PCT Pub'n No. WO2005104996; Jun. 28, 2006; WIPO; Geneva, Switzerland; all pages.
World Intellectual Property Organization; Written Opinon of the International Searching Authority for PCT Pub'n No. WO2005104996; Sep. 12, 2005; WIPO; Geneva, Switzerland; all pages.
National Institute of Industrial Property (France); Preliminary Search Report in Fench Pub. No. FR2879436; Aug. 11, 2005; National Institute of Industrial Property (France); France; all pages.
World Intellectual Property Organization; International Preliminary Report on Patentability for PCT Pub'n No. WO2006120505; Feb. 22, 2007; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; Written Opinon of the International Searching Authority for PCT Pub'n No. WO2006120505; Aug. 21, 2006; WIPO; Geneva, Switzerland; all pages.
National Institute of Industrial Property (France); Preliminary Search Report in Fench Pub. No. FR2887762; Dec. 21, 2005; National Institute of Industrial Property (France); France; all pages.
World Intellectual Property Organization; International Preliminary Report on Patentability for PCT Pub'n No. WO2007000654; Jul. 19, 2007; WIPO; Geneva, Switzerland; all pages.
World Intellectual Property Organization; International Search Report for PCT Pub'n No. WO2007000654; Mar. 14, 2007; WIPO; Geneva, Switzerland; all pages.
World Intellectual Property Organization; Written Opinon of the International Searching Authority for PCT Pub'n No. WO2007000654; Mar. 14, 2007; WIPO; Geneva, Switzerland; all pages.
National Institute of Industrial Property (France); Preliminary Search Report in Fench Pub. No. FR2891135; Jun. 27, 2006; National Institute of Industrial Property (France); France; all pages.
World Intellectual Property Organization; International Preliminary Report on Patentability for PCT Pub'n No. WO2007034310; Aug. 14, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; Written Opinon of the International Searching Authority for PCT Pub'n No. WO2007034310; Feb. 13, 2007; WIPO; Geneva, Switzerland; all pages.
National Institute of Industrial Property (France); Preliminary Search Report in Fench Pub. No. FR2893838; Aug. 4, 2006; National Institute of Industrial Property (France); France; all pages.
World Intellectual Property Organization; International Preliminary Report on Patentability for PCT Pub'n No. WO2007063398; Nov. 12, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; Written Opinon of the International Searching Authority for PCT Pub'n No. WO2007063398; Jul. 13, 2007; WIPO; Geneva, Switzerland; all pages.

(56) References Cited

OTHER PUBLICATIONS

National Institute of Industrial Property (France); Preliminary Search Report in Fench Pub. No. FR2916956; Jan. 30, 2008; National Institute of Industrial Property (France); France; all pages.

World Intellectual Property Organization; International Preliminary Report on Patentability for PCT Pub'n No. WO2008149223; Aug. 5, 2009; WIPO; Geneva, Switzerland; all pages.

World Intellectual Property Organization; International Search Report for PCT Pub'n No. WO2008149223; Oct. 31, 2008; WIPO; Geneva, Switzerland; all pages.

World Intellectual Property Organization; Written Opinon of the International Searching Authority for PCT Pub'n No. WO2008149223; Oct. 31, 2008; WIPO; Geneva, Switzerland; all pages.

World Intellectual Property Organization; International Search Report for PCT Pub'n No. WO2011080535; Jan. 24, 2011; WIPO; Geneva, Switzerland; all pages.

World Intellectual Property Organization; International Preliminary Report on Patentability for PCT Pub'n No. WO2008099277; May 29, 2009; WIPO; Geneva, Switzerland; all pages.

World Intellectual Property Organization; International Search Report for PCT Pub'n No. WO2008099277; Nov. 7, 2008; WIPO; Geneva, Switzerland; all pages.

World Intellectual Property Organization; Written Opinon of the International Searching Authority for PCT Pub'n No. WO2008099277; Nov. 7, 2008; WIPO; Geneva, Switzerland; all pages.

* cited by examiner

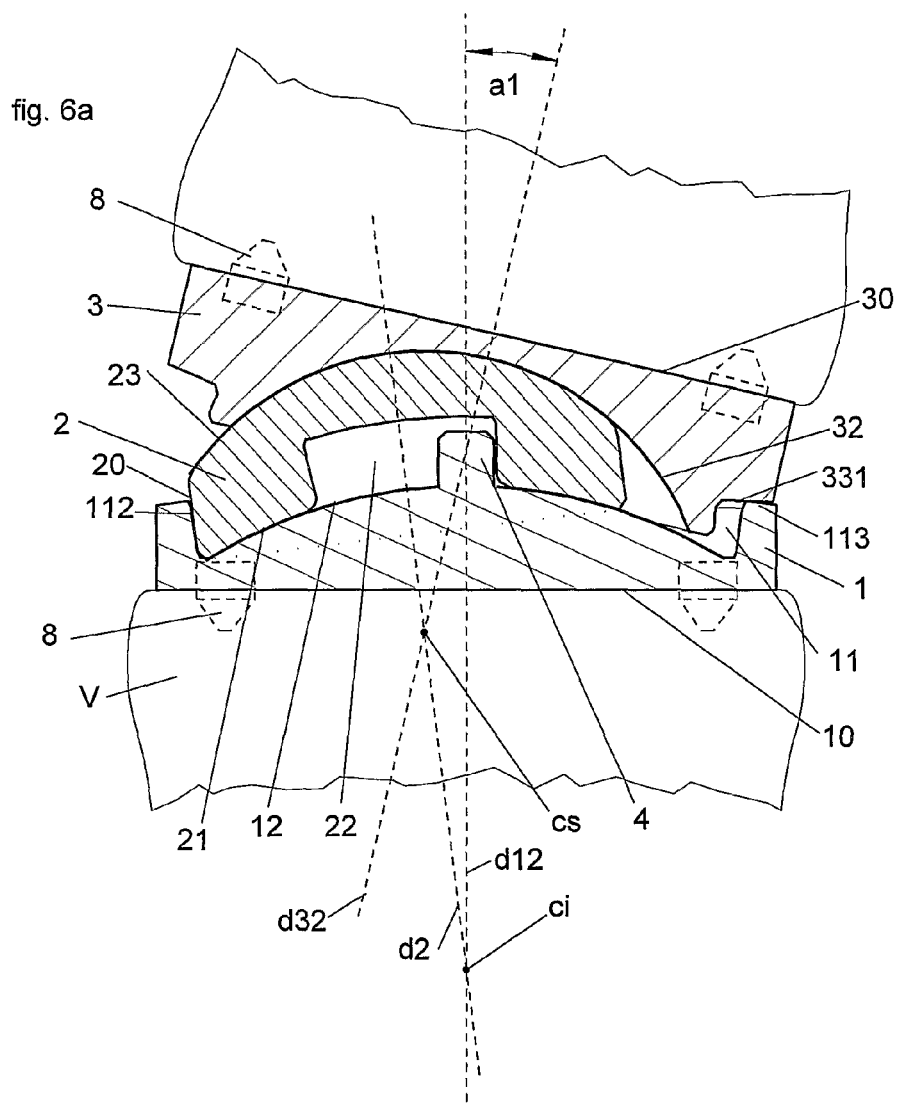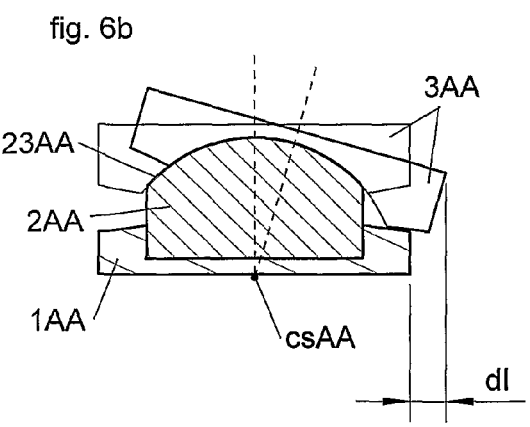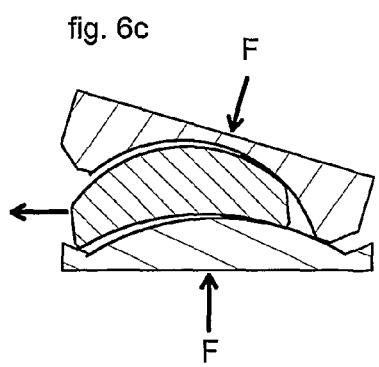

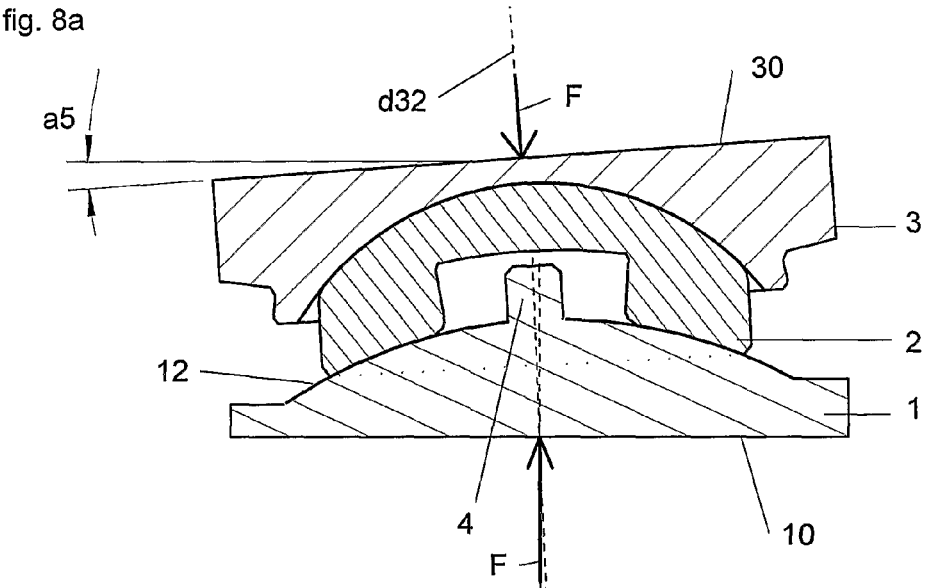
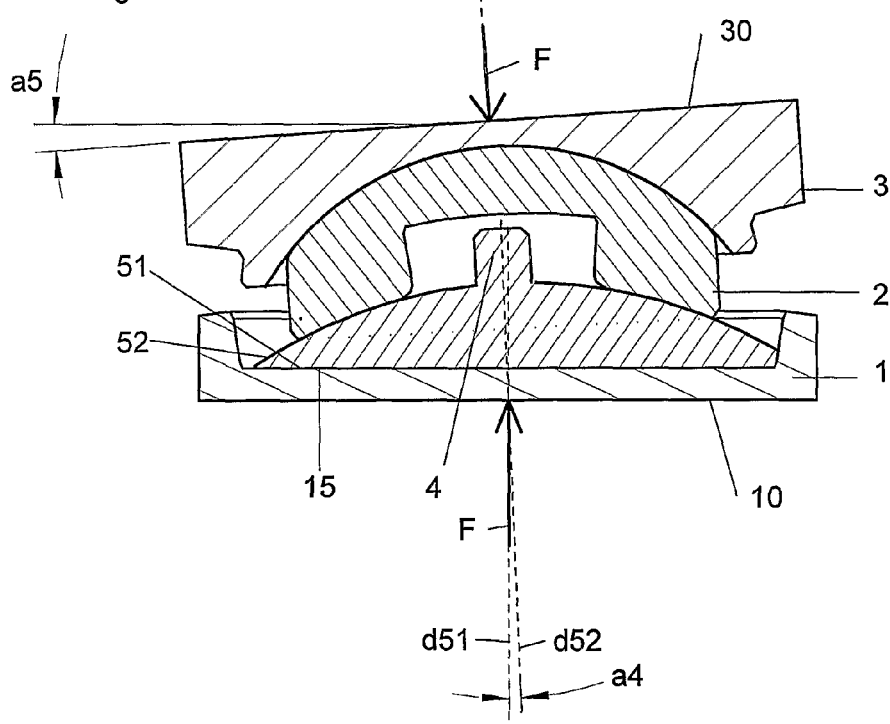

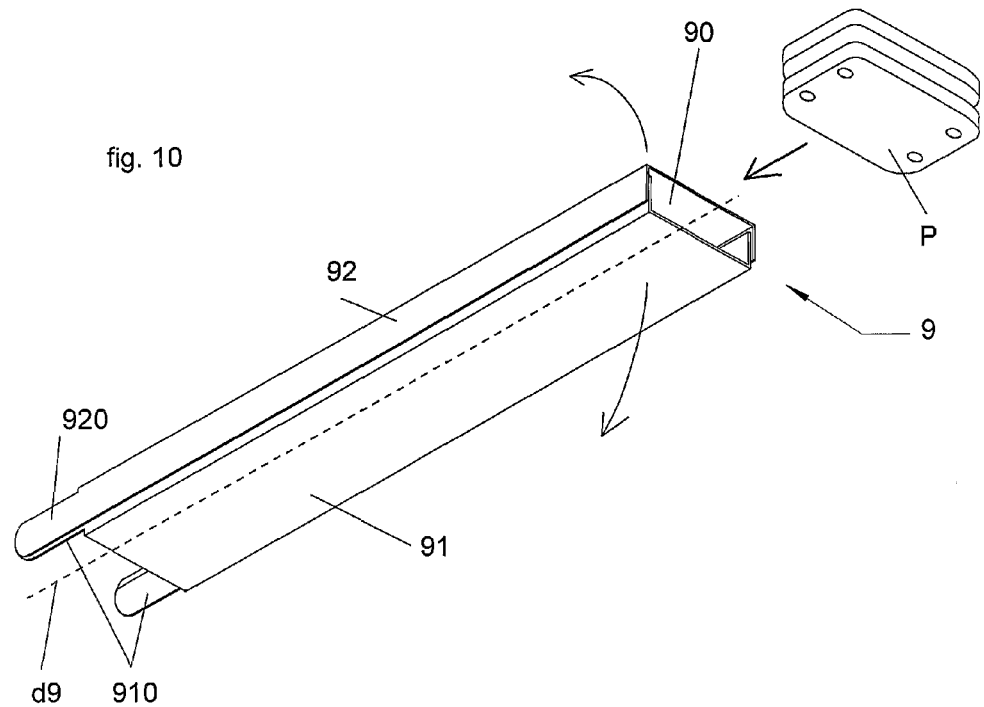
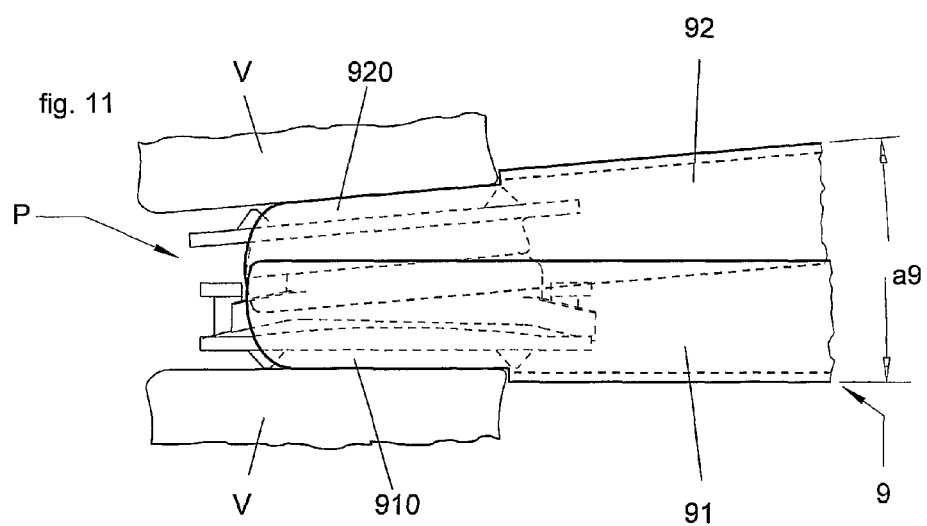

INTERVERTEBRAL DISC PROSTHESIS, SURGICAL METHODS, AND FITTING TOOLS

RELATED APPLICATIONS

The present application is a continuation of U.S. patent application Ser. No. 10/476,565 filed Nov. 4, 2003, and issuing Feb. 5, 2008, as U.S. Pat. No. 7,326,250, which is a 35 U.S.C. §371 application of PCT/IB02/002998 filed May 3, 2002, which claims priority to FR 01/05982 filed May 4, 2001. All of the foregoing documents are hereby incorporated by reference.

BACKGROUND

The present invention concerns an intervertebral disc prosthesis designed to be substituted for fibrocartilaginous discs ensuring connection between the vertebra of the vertebral column or the end of the latter.

The intervertebral discs are formed from a deformable but noncompressible element called "nucleus pulposus" containing approximately 80% water, surrounded by several elastic fibrous layers converging to maintain the nucleus, absorb part of the forces applied to the entire disc and stabilize the articulation. These elements may often be broken down or damaged by compression, displacement or wear and tear, following shocks, infections, exaggerated forces or simply over time.

The breakdown of this articulation element may cause intense pain and significant constraint in the patient. Beyond the surgery that consisted of blocking the deficient articulation and possibly purely and simply removing the damaged disc, a therapeutic route for the last twenty or so years consists of surgically replacing the defective disc with a functional prosthesis. However, the use of such a prosthesis requires a device that is not very cumbersome, that supports significant forces, or has a great sturdiness over time. Furthermore, the comfort of the patients already affected by great and acute pain makes it desirable to arrange for a prosthesis that most faithfully reproduces the natural possibilities of movements and at the same time ensures the best stability possibility to the spinal column that is sometimes already damaged.

The use of such a prosthesis therefore crucially depends on the stability that it allows the spinal column, as much during movements as during static forces or lengthy constant position.

A certain number of prostheses have been proposed with a compressible material base, with the goal of reproducing the kinematics of natural movement while reproducing its components and their characteristics of shape or plasticity, as described in the patent FR 2 124 815 which proposes a disc from elastomer material reinforced by a textile material. These devices present the drawback of a lifetime that is often too limited and also suffer from drawbacks indeed due to this elasticity. In fact, since the prosthesis is entirely compressible, a progressive sliding of the prosthesis may be produced relative to the vertebra between which it is placed, which too often leads it to leave its housing. The addition of anchoring pins does not allow sufficient remedy for this problem, because the micromovements permitted by the compressibility of the material of the prosthesis also include a vertical component, which too easily allows the pins to leave their housing with each movement.

Among the prostheses nor resting on the deformation of materials, a type of prosthesis frequently used is described by the patent DE 30 23 353 and is formed of a nucleus with the shape of a biconvex lens forming articulation between two plates each presenting a cavity with a shape approximately complementary to the nucleus in their centre and on their perimeter a shoulder retaining this nucleus. This arrangement presents the advantage by comparison to a more limited ball-and-socket joint of using significant contact surface, which largely decreases the wear and tear.

To incline one with the other on one side, the plates are articulated by their internal cavity on the edge of the nucleus of the side in question, but according to a rotation movement which, on the other side makes their edges move apart more than they were at rest. This separating has a tendency to detach the vertebral plates on which they are supported, which damages the surface of the vertebra at the sites where the plates have just anchored and again allows progressive displacement with risk of complete ejection of the prosthesis.

Another type of prosthesis described in patent FR 2 659 226 consists of an upper plate presenting a concave face that comes to slide on a nucleus in the form of a segment of a sphere, this nucleus being immobilized in a cavity of the lower plate. In this case, the rotation is done more satisfactorily from the point of view of space of the plates, but the sliding of the upper plate on a sphere whose centre is located on the exterior of the prosthesis also causes lateral displacement which may be harmful as much to the kinematics of movement as to the organs present in the vicinity.

A solution is proposed in the patent FR 2 730 159 in the form of a nucleus presenting two spherical faces, oriented in the same direction, and with different radius. The nucleus with cylindrical exterior slides on a convex surface belonging the lower plate and itself presents a convex surface on the top, on which the upper plate slides. Because the nucleus is movable horizontally, it is in a position to move apart from one side when the plates approach the other. However, this device presents the drawback of risking the complete ejection of the nucleus outside the prosthesis, this drawback also existing in the device described by the patent DE 30 23 353).

In the goal of limiting the risks of ejection of the nucleus, the patents WO 00 53 127, as well as U.S. Pat. No. 5,401,269 and U.S. Pat. No. 4,759,766 propose to provide a translation stop, produced in different ways.

In certain variants, a translation stop is disclosed in the form of a relief protruding from one contact surface of the nucleus and movable in a recess in the plate or inversely. This type of internal stop is therefore located on the interior of a contact or support surface between nucleus and plate, and therefore decreases the available surface considerably. This decrease in support surface increases the stresses undergone by the materials, therefore the risks of wear and tear or strain in creep or exceeding elastic limits. The separation between the support surface and housing receiving the stop may also risk marking the piece which is supported above and damaging the latter.

In certain cases, such a central stop is provided with a noncircular shape, which in a certain extent allows the rotations of the nucleus to be limited relative to the plate that provides it. However, this noncircular forms additional constraint which again limits the surface available for support. Furthermore, the angles of this shape themselves form fragile zones, which only ensures low sturdiness to this stop operation in rotation.

In other variants, a collar protrudes from the nucleus and surrounds it in the space between the two plates. In its exterior part this collar widens at a certain height along the axis of the spinal column towards each of the plates, which forms two interior borders that may be supported on the exterior border of contact surfaces of these same plates. However, this type of external peripheral stop presents certain drawbacks, in particular in terms of obstruction.

In fact, the configuration of this collar represents considerable vertical obstruction (along the spinal column axis) and the contact surfaces of the plates must also present a certain height to be able to stop this collar in translation. Furthermore, the peripheral shape of this type of stop also occupies considerable radial space, in particular in a section plane where the spinal column presents the smallest width, as in sagittal plane. Given the limited space available in the disc, or intervertebral, space, this obstruction may occupy a space that would be useful for the configuration of the rest of the prosthesis, which may limit the results in terms of kinematics or reliability.

Moreover, this type of external peripheral stop requires a nucleus with biconvex shape to be used, to allow for provision of sufficient height for the contact surfaces of the plates to form an exterior border usable by this stop. Therefore, this type of stop is difficult to produce for a nucleus presenting one or more concave surfaces, while such forms of nucleus may allow the kinematics of the prosthesis to be made more comfortable with use by the patient.

In the case where the contact surfaces between nucleus and plates are not circular, such a collar may also be able to limit the clearance in rotation of the nucleus relative to the plates, for example by peripheral contact between two concentric ellipses and with different radii. However, such contact is done according to a very tight angle between the surfaces being supported on each other, which makes the position of this limit not very precise and increases the risks of wear and tear or blockage by clamping. Furthermore, the clearance in rotation permitted by such kinematics is directly dependent on the clearance permitted in translation, and may not be chosen independently of the latter during design of the prosthesis.

SUMMARY

A goal of the invention is to propose a prosthesis allowing the spinal column better stability by a greater precision and sturdiness in relative positions of pieces that compose it.

This goal is reached by a vertebral prosthesis device according to claim 1.

Moreover to ensure stability of the spinal column after fitting such a prosthesis, the damages undergone by the spinal column because of the different pathologies leading to deciding to fit a prosthesis sometimes make useful the re-establishing of stability or posture that the elasticity of the spinal column no longer allows to be provided. According to the pathologies and the history of the patient, it may then be indicated to induce a certain angular correction in the configuration of the intervertebral space for example in the sense of lordosis or that of kyphosis.

Certain types of existing prostheses use a variation in thickness of one of the plates to induce such a correction. Such a correction is not however always very stable, in particular because the position of supports of the nucleus on the plates varies too much during movements.

Another goal of the invention is therefore to propose a prosthesis allowing the prosthesis better stability by the re-establishment of posture adapted to the kinematics of movements that it produces.

This goal is reached by a vertebral prosthesis device according to claim 5.

Additional developments of the invention are described in the dependent claims.

The invention with its characteristics and advantages will be more clearly evident with reading the description made in reference to the attached drawings in which:

BRIEF DESCRIPTION OF THE DRAWINGS

FIG. 6a represents a sectional side view of the prosthesis device according to the invention in a variant with central, annular and incline stop, in maximum incline position;

FIG. 6b represents a sectional side view of a prosthesis according to the prior arts where the nucleus presents a fixed position;

FIG. 6c represents a sectional side view of a prosthesis according to the prior arts where the nucleus is movable and is ejected under the load during a force in the maximum incline position;

FIGS. 8a and 8b represent sectional side views of the prosthesis device according to the invention according to a variant with inclined axis, including an annular stop and a central stop incorporated in the contact surface supporting the nucleus, in the case of a single piece lower plate and an added block, respectively.

FIG. 10 represents a perspective view of a device according to the invention for fitting such a prosthesis;

FIG. 11 represents a perspective view of a device according to the invention for inserting such a prosthesis, in position during the introduction laterally of the prosthesis between two vertebrae;

DETAILED DESCRIPTION

Figure 1:
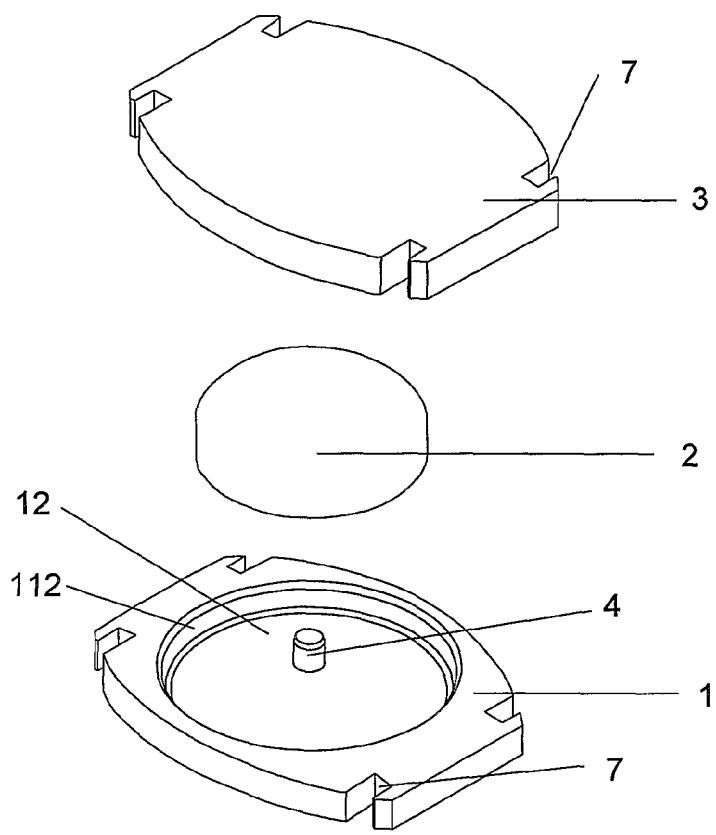
FIG. 1 represents an exploded view in perspective of a prosthesis according to the invention, in a version including a convex lower plate and providing a central and annular stop.
Figure 2:
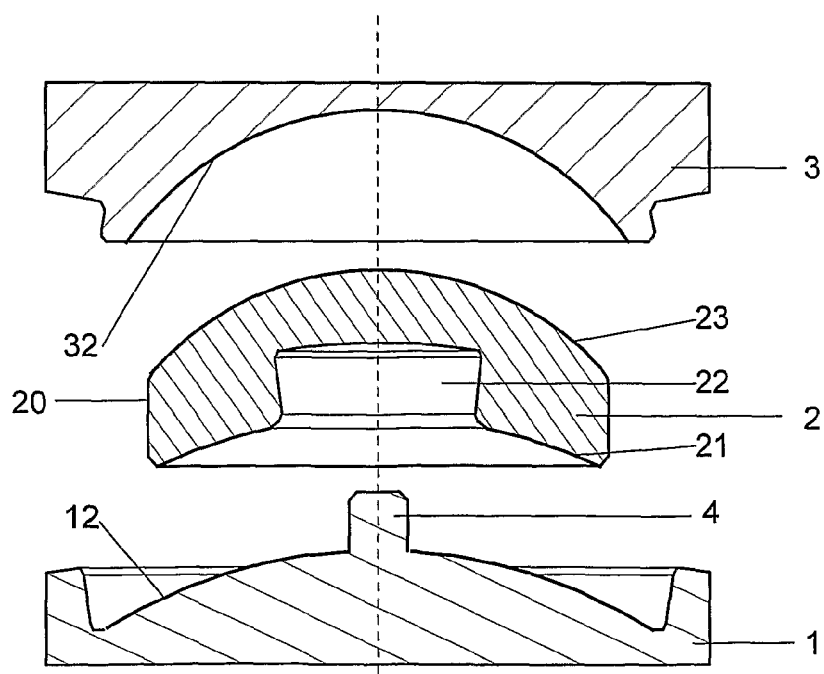
FIG. 2 represents an exploded sectional view of a prosthesis device according to the invention in the same variant.

A prosthesis according to the prior art disclosed by the patent FR 2 659 226, consisting of a concave upper plate (3AA) sliding on a nucleus (2AA) presenting a spherical upper cap (23M) itself immobilized in a housing of the lower plate (1AA), is represented in FIG. 6b; in horizontal position and in maximum incline position. Because the centre of the sphere (csAA) providing the contact surface with the nucleus is located outside this same upper plate (3AA), its incline is combined with considerable lateral displacement (d1). This displacement creates a break in the continuity of the vertical profile of the vertebral column which may hamper the overall functionality of the movement and risk damaging the tissues surrounding the vertebrae, such as ligaments and spinal marrow, which may be immediately or in the long run.

A prosthesis according to the prior art disclosed by the patent FR 2 730 159, represented in FIG. 6c, consists of a movable nucleus with two spherical surfaces oriented in the same direction, that may be laterally displaced between two plates and may allow incline without lateral displacement. In the extreme position, however, the nucleus is only kept on the exterior side by the furthest border of the spherical surface of the upper plate. Since this edge itself is already raised, there is a great risk that too high a vertical pressure or a horizontal parasitic force causes ejection of the nucleus towards the exterior of the prosthesis, causing intense pain and risks of immediate damage for the tissues surrounding the vertebral column, such as ligaments or spinal marrow.

In an embodiment represented in FIG. 6a, a prosthesis according to the invention consists of a lower plate (1) being articulated with an upper plate (3) around a nucleus (2) presenting two spherical sliding surfaces with the same orientation on both faces. The lower surface (21) of the nucleus (2) is concave and slides on a complementary convex surface (12) provided by the upper face, known as internal, of the lower plate (1). The upper surface (23) is convex and slides on a complementary concave surface (32) provided by the lower face, known as internal, of the upper plate (3). In this embodiment, the radius of the lower contact surface (21) of the nucleus (2) is a radius greater then that of its convex upper surface (23), the centres of the spheres providing its two contact surfaces being located on the same axis of symmetry (d2) of these two surfaces. On their side, the two plates present contact surfaces (12, 32) the axes of symmetry (d12, d32) of which are perpendicular to their external faces (10, 30). The horizontal displacement part of the nucleus in one direction, due to the rotation on the upper sliding surface around its centre (cs), is compensated by a rotation of the nucleus on its lower sliding surface around its centre (ci) which induces horizontal displacement of the nucleus (2) and therefore of the centre (cs) of the upper sliding surface. The radii of the two spheres providing these sliding surfaces (12, 21, 23, 32) are determined so as to modify the lateral displacement of the plates by comparison with each other during their incline. In one embodiment, the radii of these sliding surfaces (12, 21, 23, 32) may be chosen so that the movement of the plate is reduced to an incline accompanied with a possible vertical component but without horizontal displacement of the upper plate relative to the lower plate.

To avoid any risk of ejection of the nucleus (2) during forces in the inclined position, the latter is kept in its clearance by a central stop, formed for example by a cylindrical block (4) protruding from the convex surface of the lower plate and cooperating with edges of a recess (22) arranged in the centre of the contact surface (21) of the lower concave surface of the nucleus.

In one embodiment (FIG. 6a) the lower plate also presents on its upper face an approximately cylindrical cavity (11) in which the edges (112) protrude from the contact surface (12) with the nucleus (2), and cooperate with the approximately cylindrical perimeter (20) of this nucleus to ensure an operation of annular stop for it while limiting its movement towards the exterior of the contact surface (12) that provides it.

In one embodiment (FIG. 6a) the internal surfaces of the plates, on their parts (113, 331) exterior to the sliding surfaces, present a form capable of cooperating among themselves to limit by stop the incline of the plates with each other at a determined angle (a1).

Figure 7:
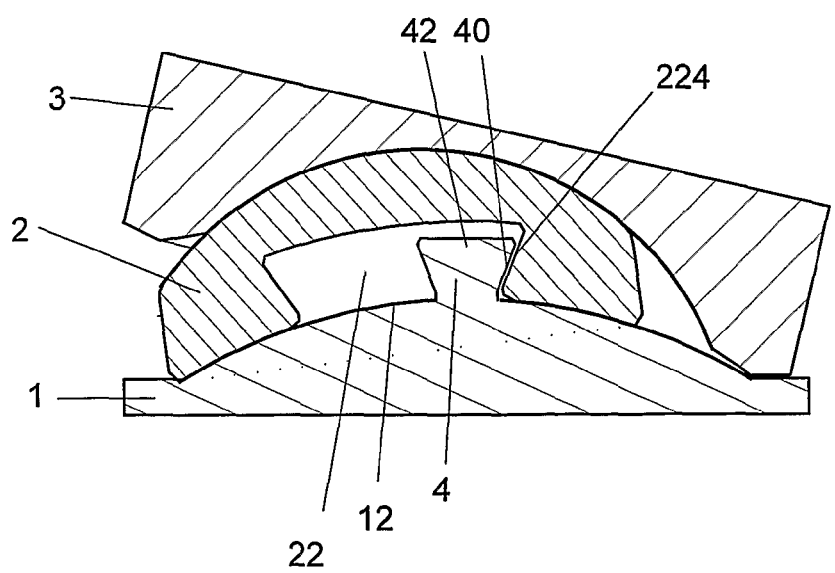
FIG. 7 represents a sectional side view of the prosthesis device according to a variant without annular stop and where the central stop presents a vertical section in the form of a dovetail, in maximum incline position.

In one embodiment represented in FIG. 7, the stop (4) is provided by the convex surface (12) of the lower plate (1) and presents approximately the shape of an inverted cone, that is, its section is greater in its end (42) opposite the surface (12) that provides it. By presenting an undercut shape, the interior surface (224) of the recess (22) cooperates with the exterior surface (40) of the stop (4) to limit the raising of the nucleus when the latter is in furthest position against this stop (4).

According to the criteria connected for example to the resistance of the materials, to the wear and tear or to the kinematics sought, the different shapes and dimensions intervening in the stop mechanisms, for example exterior (FIGS. 9a and 9b), annular, central or incline, could be determined so as to coordinate the order of arrival at stop of the different parts. These shapes and dimensions could be determined for example, so that the pieces reach stop at the same stage of movement, for example determined by angular incline (a1) between the lower (1) and upper (3) plates.

In an embodiment illustrated in FIGS. 7 and 8a, the annular stop operation is used very little or not at all, which allows the vertical obstruction of the prosthesis to be decreased.

Figure 3:
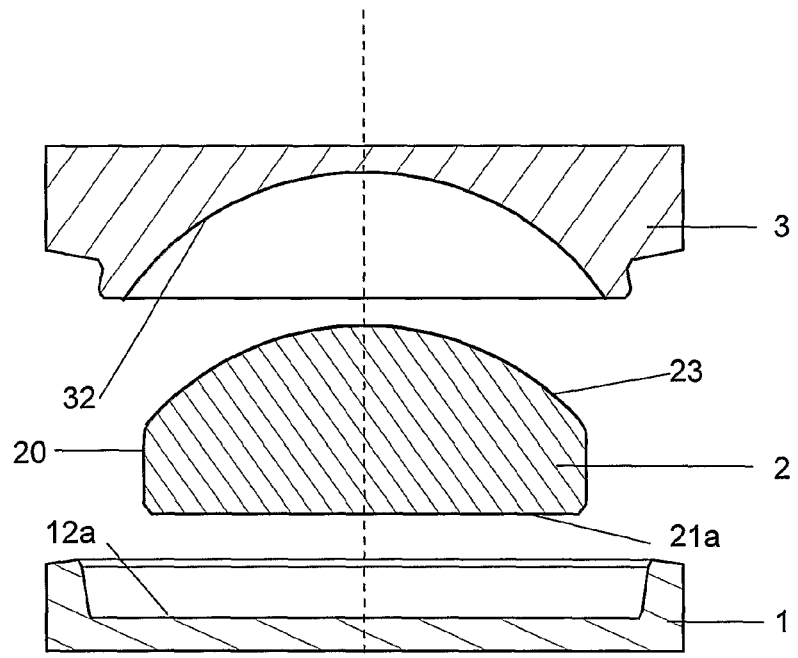
FIG. 3 represents an exploded sectional view of the prosthesis device according to the invention in a variant including a nucleus with flat lower surface and lower plate presenting an annular stop.

In an embodiment presented in FIG. 3, the lower surface (21a) of the nucleus (2) may be approximately flat, and then slide on a contact surface (12a) of the lower plate (1), also approximately flat. In this embodiment, the flatness of the contact surface (12a) of the lower plate allows the edges (112) of this plate that protrude from this surface to be particularly effective in their role of annular stop. Therefore, it is possible to manage without the central stop and thus to increase the common contact surface between the lower plate and the nucleus, which on the one hand, decreases the wear and tear of the pieces and on the other hand, the risk of marking the surface of the plate with placement of the contour of the recess (22, FIG. 6a) in which is accommodated the central stop (4, FIG. 6a) in other embodiments.

Figure 4:
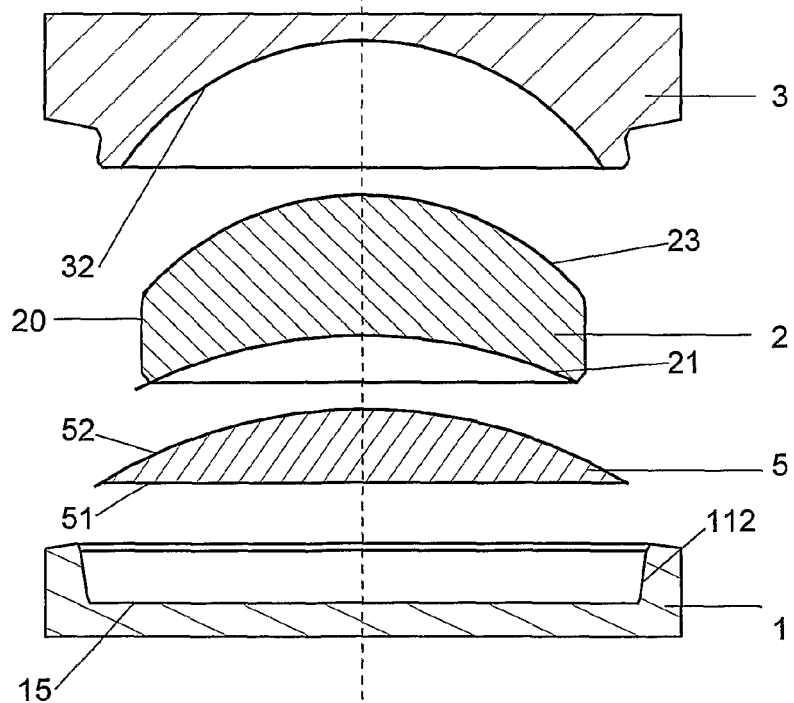
FIG. 4 represents an exploded sectional side view of the prosthesis device according to the invention in a variant including a nucleus with concave lower face, an added block and a lower plate with annular stop.

In an embodiment represented in FIG. 4, the lower plate (1) presents an approximately cylindrical cavity (11) on its upper face the flat bottom (15) of which receives an intermediate piece called block (5). This piece is immobilized in the cavity (11) for example by the edges (112) of this cavity and presents on its upper face a convex surface (52) on which the lower concave surface (21) of the nucleus slides. This embodiment with the convex surface (52) on which the nucleus slides for example allows the good qualities of the surface necessary for the fluidity of movement and longevity of the prosthesis to be obtained more easily and at less cost. It also allows several models to be provided with blocks (5), of different shapes or qualities, that can be chosen in advance or at the time of the surgery according to applications with the same model of lower plate.

Figure 5:
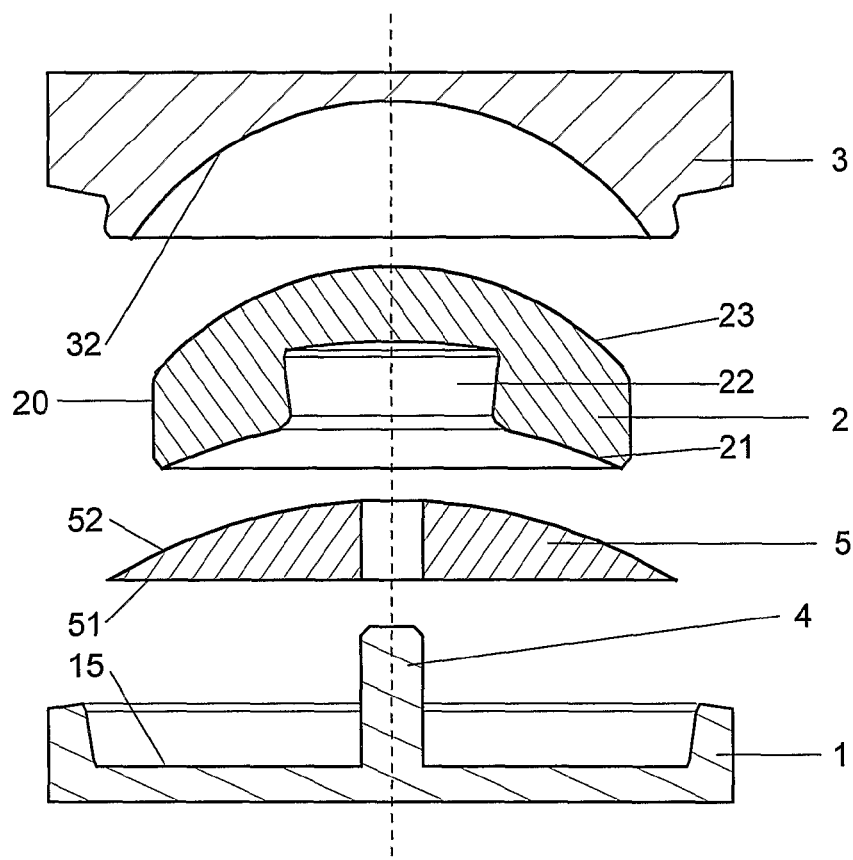
FIG. 5 represents a sectional exploded side view of the prosthesis device according to a variant including an added block allowing a central stop to appear and a flat lower plate presenting an annular stop.

In an embodiment represented in FIG. 5, the lower plate (1) receives a block (5) in an approximately cylindrical cavity (11) presenting a vertical perforation that the stop (4) integral with the lower plate crosses. On its upper surface, this block supports a convex surface (52), on which the nucleus (2) and upper plate stack rests.

As a variant, the stop (4) may be integral with the block (5) on its convex contact surface (52)(FIG. 8b).

Within the goal of obtaining at rest a corrective effect of the relative position of two vertebrae, the prosthesis may be produced in a variant where the axes of symmetry of the contact surfaces (12, 15, 52, 21, 23, 32) or support (10, 30) of one or more pieces are not merged. The pressure (F) exerted by the vertebrae on the two plates in the directions perpendicular to their external surfaces (10, 30) will then have the tendency to induce and continuously maintain an incline (a3, FIGS. 8a, 8b et 8c) between these plates (1, 3), that is not zero, for example in the sense of lordosis.

An embodiment of such a variant is represented in FIG. 8a where the axis of symmetry (d12) of the contact surface (12) of the lower plate (1) forms an angle (a2) determined with a direction (d10) perpendicular to the external surface of this same lower plate, while the axis of symmetry (d32) of the internal contact face (32) of the upper plate (3) is perpendicular to the external surface (30) of this same upper plate (3). The lower contact surface of the upper plate (3) presents an axis of symmetry parallel to a direction perpendicular to the support surface (30) of the ¶ of this same upper plate (3).

In another variant according to the same principle represented in FIG. 8b, a device is used that includes a lower plate (1) providing a block (5) the upper contact surface of which (52) presents an axis of symmetry (d52) forming an angle (a2) determined with a direction (d51) perpendicular to its lower face (51). The internal contact surfaces (15, 32) of the lower (1) and upper (3) plates present axes of symmetry perpendicular to the support surface (10, 30) of their respective external faces. Thus, at the time of the surgery it is possible to choose between several blocks (5) with different inclines, according to the desired degree of correction. This block (5) could be maintained fixed around an axis perpendicular to the lower plate (1) by any known means (not represented) such as wedge, grooves or complementary accidents of shape between the block (5) and the lower plate (1) that provides it.

Figure 8C:
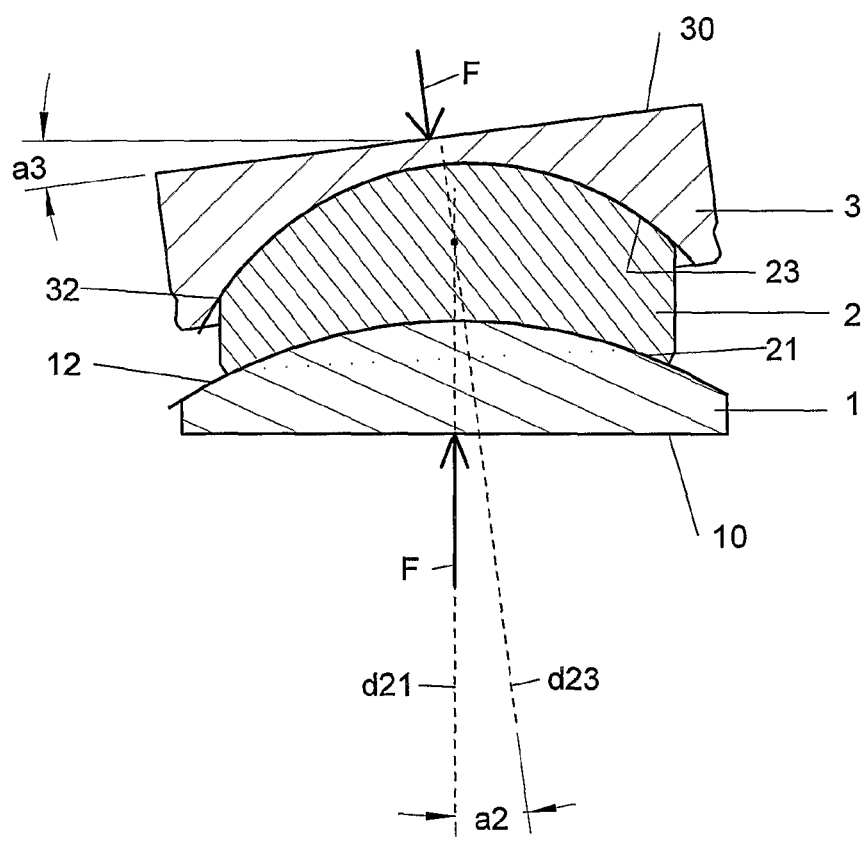
FIG. 8c represents a sectional side view in a sagittal plane of the prosthesis device according to the invention according to a variant with a corrective nucleus presenting two faces in which the contact surfaces are not parallel.

In another variant according to the same principle, represented in FIG. 8c, it is the nucleus (2) that presents two contact surfaces (21, 23) the axes of symmetry of which (d21, d23) form a determined angle (a2) between them. The internal contact surfaces (12, 32) of the lower (1) and upper (3) plates present axes of symmetry perpendicular to the support surface (10, 30) of their respective external faces. The angular correction (a3) induced by the nucleus (2) could then be kept constantly in the desired direction relative to the body of the patient by a rotation stop mechanism (not represented in FIG. 8c) of this same nucleus, such a mechanism being described later (FIGS. 9a and 9b).

In one embodiment the device according to the invention presents an exterior stop mechanism, located outside the perimeter of the contact surfaces of the nucleus (2).

Figure 9A:
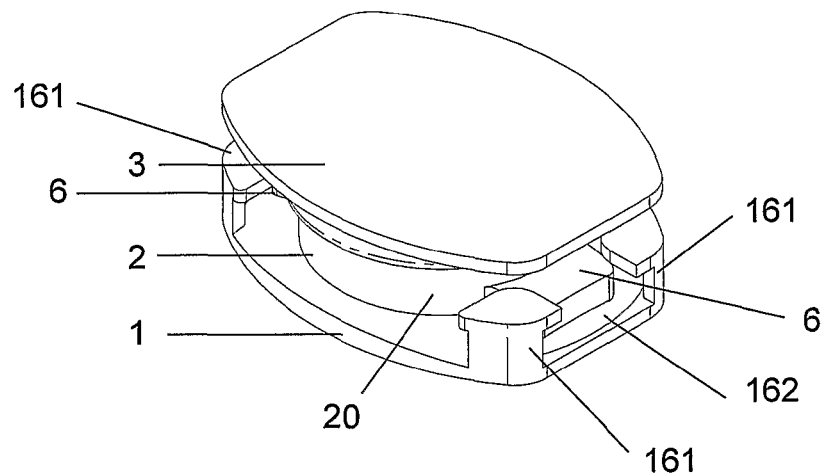
FIG. 9a represents a perspective view of the prosthesis device according to the invention according to a variant with two stops exterior to the nucleus, held in a housing between pillars integral with the lower plate.
Figure 9B:
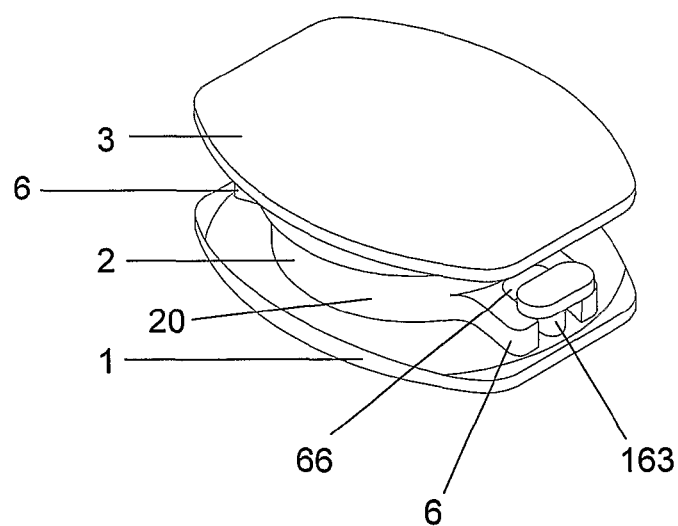
FIG. 9b represents a perspective view of the prosthesis device according to the invention according to a variant with two stops exterior to the nucleus, each holding a pillar integral with the lower plate between its arms.

In a variant represented in FIG. 9a, this mechanism is formed of two protruding parts (6) protruding from the cylindrical exterior surface of the perimeter of the nucleus (2) in opposite directions. Each of these protruding parts is held in a housing (162) delimited by two pillars (161) integral with the lower plate (1). These pillars cooperate with the protruding part (6) or with the surface (20) of the perimeter of the nucleus or both for limiting the movements of this same nucleus in translation as in rotation parallel said plate. The housing is sufficiently large to allow small displacements of the nucleus required for the kinematics of the device, while being sufficiently narrow so that this same nucleus and the lower plate are adjacent in certain positions, for example, positions of maximum incline of the spinal column. The protruding part (6) or perimeter surface (20) of the nucleus (2) then cooperates with the pillars (161) of the lower plate to retain this same nucleus and avoid any lateral ejection.

The pillars (161) present a larger section at the end than at the base, thus limiting the raising of the nucleus.

In another operating variant according to the same principle and represented in FIG. 9b, this mechanism is formed of two protruding parts (6) protruding from the cylindrical exterior surface (20) of the perimeter of the nucleus (2) in opposite directions. Each of these protruding parts presents two arms delimiting a housing (66) which hold a pillar (163) integral with the lower plate (1). The pillars (163) present a larger section at their end than at their base.

These embodiments of stop (9a and 9b) may allow the central stop to be disposed of and to thus increase the contact surfaces which decreases the wear and tear. These types of stop (6) are also particularly valuable because of the limitation of the movements of the nucleus in rotation along an axis approximately parallel to the axis of the spinal column. In fact, this limitation makes it possible to use a corrective nucleus in which the contact surfaces present axes of symmetry that are not parallel, while maintaining in them the correction in a constant direction relative to the body of the patient.

In an embodiment represented in FIG. 6a, the lower (1) and upper (3) plates receive means for bony anchoring on their external face, designed to immobilize the prosthesis between the vertebrae or adjacent elements of the spinal column. These anchoring means may be pins (8) or wings presenting a small cross section at their end away from the plate that provides them. These pins then are embedded or are impacted by punching in the material of the bony elements (V) between which the prosthesis is fitted, for example under the effect of the pressure exerted by the ligaments when the tools are withdrawn, the tools that kept the vertebrae separated. Driving in the pins in the material of the bony element (V, FIG. 6) then prevents the prosthesis from sliding outside its site.

In an embodiment represented in FIG. 1, the plates (1, 3) present one or more accidents of shape such as notches (7) or perforations (not represented) enabling catching of a grasping tool to remove the prosthesis from its site in case of need. The lower plate (1) presents a convex upper contact surface (12) providing a central stop (4) and a cavity presenting edges (112) forming an annular stop.

In an embodiment represented in FIG. 10, an insertion device according to the invention is presented in the form of an element (9) called insertion guide, presenting an internal channel (90) approximately rectangular in section in which the prosthesis (P) can slide. This channel (9) is formed from two semi-guides (91, 92) with a cross section in the shape of a "U", arranged inversely and fitted into each other. At one of the ends, this guide (9) presents one or more parts called support blocks or edges (910, 920) protruding along its longitudinal axis (d9). These support blocks (910, 920) form an extension of the walls of the channel called vertical (9) that form the small sides of the rectangular section of the channel (9).

In an application method illustrated in FIGS. 10 and 11, the fitting of the prosthesis device according to the invention is carried out according to the following steps:

separating the vertebrae with the aid of known instruments, for example distraction tools;

sliding the insertion guide (9) around the distraction tools so as to introduce the support edges (910, 920) between the vertebrae (V);

release and extraction of the distraction tools, the vertebrae being kept spread apart by the support edges of the insertion guide;

introduction of the prosthesis ready for fitting into the channel, and sliding to near the spinal column;

adjustment of the incline of the prosthesis according to conformation of the space available between the vertebrae with possible separating of the two parts (91, 92) of the channel according to a corresponding angle (a9) to help with this adjustment;

positioning of the prosthesis in the intervertebral space by pushing by the interior of the channel;

extraction of the support blocks (910, 920) of the channel outside the intervertebral space and impacting blocks for bony anchoring in the vertebrae (V).

In an embodiment illustrated in FIGS. 12a to 14, the instrumentation used for fitting the prosthesis according to the invention comprises an insertion guide (93) provided with an internal channel (90). This channel (90) presents an approximately rectangular cross section, or with a shape approximately complementary to the exterior profile of the prosthesis. This internal channel (90) is provided with dimensions and shape adequate for allowing the prosthesis to pass and to guide from one of its ends to the other, in a position and along a displacement approximately parallel to the external faces of its plates (1, 3). According to the applications, the channel (90) of the insertion guide (93) may include scallops in its walls opposite plates of the prosthesis. Such scallops make it possible to allow the anchoring means (8, 81) to pass provided by the plates of the prosthesis, while guiding the latter sufficiently precisely in the channel. In the embodiment illustrated here these scallops have the shape of grooves (934, 936) along the axis (d9) of the channel provided by the internal walls of the channel opposite plates (1, 3).

At one of its ends, called the working end, the walls (931, 932) of the channel (90) perpendicular to the plates of the prosthesis, that is, located in the plane containing the axis of the spinal column, are extended along the axis (d9) of this channel over a distance determined so as to protrude relative to the walls of this same channel that are parallel to the plates of the prosthesis. Since these extensions thus form the protruding parts, or support edges, that may be inserted in the intervertebral space to maintain the separation of the plates from the two vertebrae surrounding this space.

The height of these support edges (931, 932) is determined so as to maintain adequate space for allowing the introduction of the prosthesis and its anchoring means (8, 81), according to the method of anchoring provided. If the anchoring means are formed from sockets (8) or wings (81) before being introduced freely in the space, the support edges will have sufficient height to allow the height of these sockets or wings to pass. If the anchoring means are formed from wings having to penetrate the vertebral plates by a hollowed trench in the surface of these plates and opening laterally, the height of these support edges could be sufficiently low to allow the height of the prosthesis to pass but not the wings.

During surgery for fitting such a prosthesis, the surgeon begins by removing the vertebral disc or its debris, and then uses distraction tools to increase the disc space available between the two vertebrae having to receive the prosthesis. Such tools are often formed with an elongated handle providing a flat part at the end. This flat end is introduced between the vertebrae, then it is made to pivot to increase the separation of the vertebrae.

In the instrument according to the invention, the internal channel (90) of the insertion guide (93) is provided to be able to be threaded around such distraction tools, once they are in place between the vertebrae. Once brought near the spinal column while surrounding the distraction tools, the insertion guide is pushed so as to introduce its edges (931, 932) between the vertebrae, in a plane approximately parallel to the spinal column. The distraction tools may then be removed from the spinal column by making them slide in the channel (90) of the insertion guide, while the height of the support edges preserves sufficient space between the vertebrae to allow fitting of the prosthesis. In the embodiment illustrated here, the insertion guide (93) presents means for interlocking with a guide assembly tool (94), used to bring it near the spinal column and facilitating its fitting. This guide assembly tool (94) is also usable for removing the insertion guide and its support edges, and allowing the vertebrae to tighten on the prosthesis, once the latter is in place.

Figure 12A:
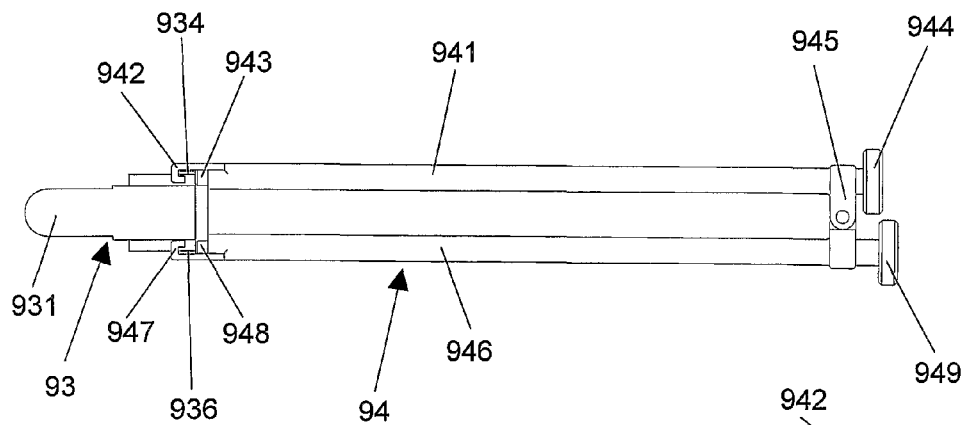
FIG. 12 represents a perspective view of an assembly tool with an insertion guide according to an embodiment of the invention.
Figure 12B:
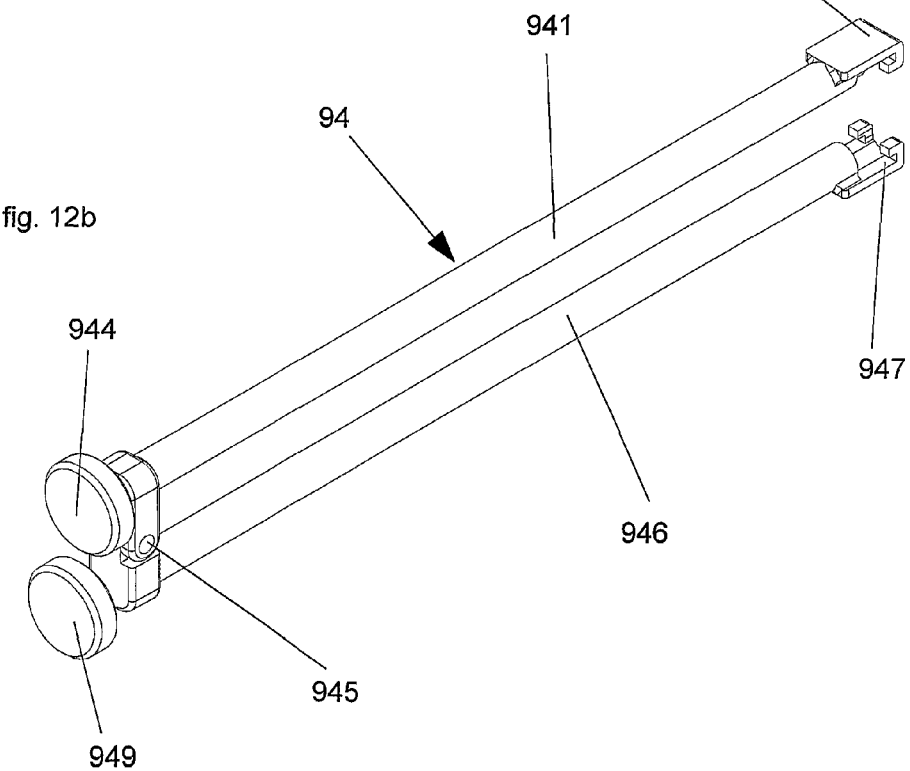
Figure 13:
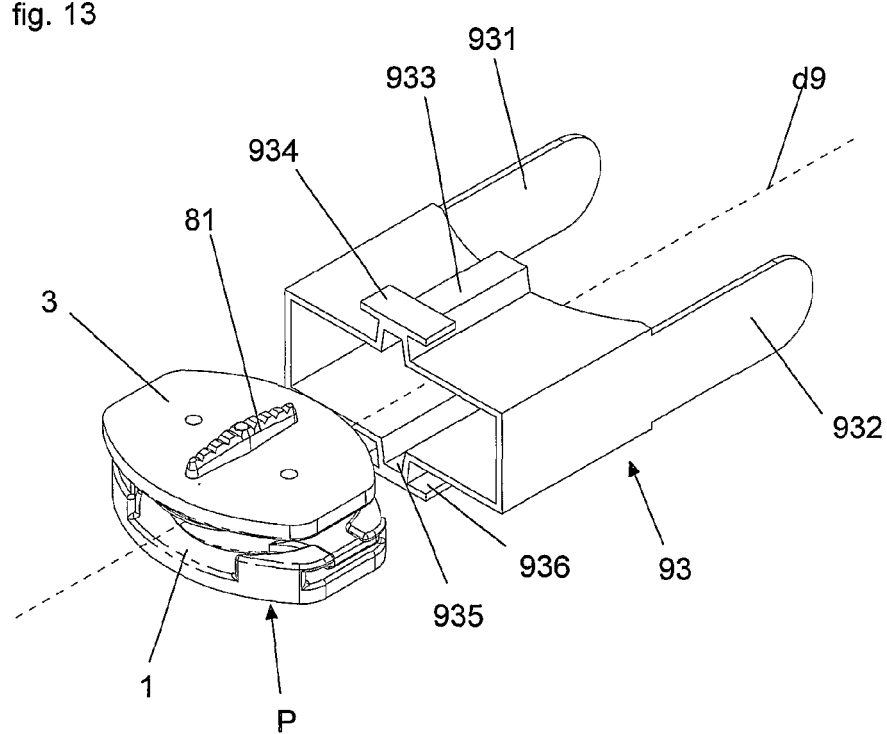
FIG. 13 represents a perspective view of a prosthesis according to the invention, presented at the entrance of the insertion guide of the invention.

Such a guide assembly tool (94) is illustrated in FIGS. 12a and 12b. This tool (94) consists of two elongated tubes (941, 946) articulated to each other by means (945) located at one end, called assembling, of this tool. These two elongated tubes at their end located opposite the assembling end, each provide interlocking means for insertion guide (93). These interlocking means may comprise, for example, a hook (942, 947) on each tube (941, 946) the opening of which is located opposite the other tube. When the guide assembly tool (94) is approached by the insertion guide (93), the fact of tightening the tubes to each other around their articulation makes it possible for each hook (942, 947) to tightly encircle a tongue (934, 936) in the shape of a "T" protruding on each groove (933, 935) of the insertion guide. Within and in the axis of each tube (941, 946) is found a rod (943, 948) that may be displaced longitudinally relative to the tubes by screwing means comprising a screwing wheel (944, 949). The screwing of these wheels causes the advance of the rod in the tube and the end of the rod opposite the screwing wheel then comes to lean and block the tongue (934, 936) of the insertion guide (93) within the hook (942, 947) provided by the tube receiving this same rod. This blockage thus makes it possible to interlock the guide to its assembling tool sufficiently stably to make it possible to position said guide around the distraction tools at the spinal column.

These means (934, 936) of interlocking the insertion guide (93) or others provided by said insertion guide also make it possible to guide and interlock means of approach (95) to this insertion guide. These means (95) of approach include means for positioning the prosthesis, these means of positioning being provided to position and maintain the assembled prosthesis in a determined position relative to these means (95) of approach even in the absence of the insertion guide (93). This positioning of the prosthesis on the approach means makes it possible for the interlocking of the approach means and the insertion guide to put the prosthesis in a position making it possible for it to be easily displaced from these same means or approach up to in the internal channel (90) of the insertion guide (93). Thus, it is possible to prepare the prosthesis in the approach means (95) independently of the rest of the operation. Then it is possible to fit the insertion guide on the spinal column without being preoccupied with the prosthesis, then easily and rapidly inserting this prosthesis in the insertion guide (93) while the latter is already in position against the spinal column.

Figure 14:
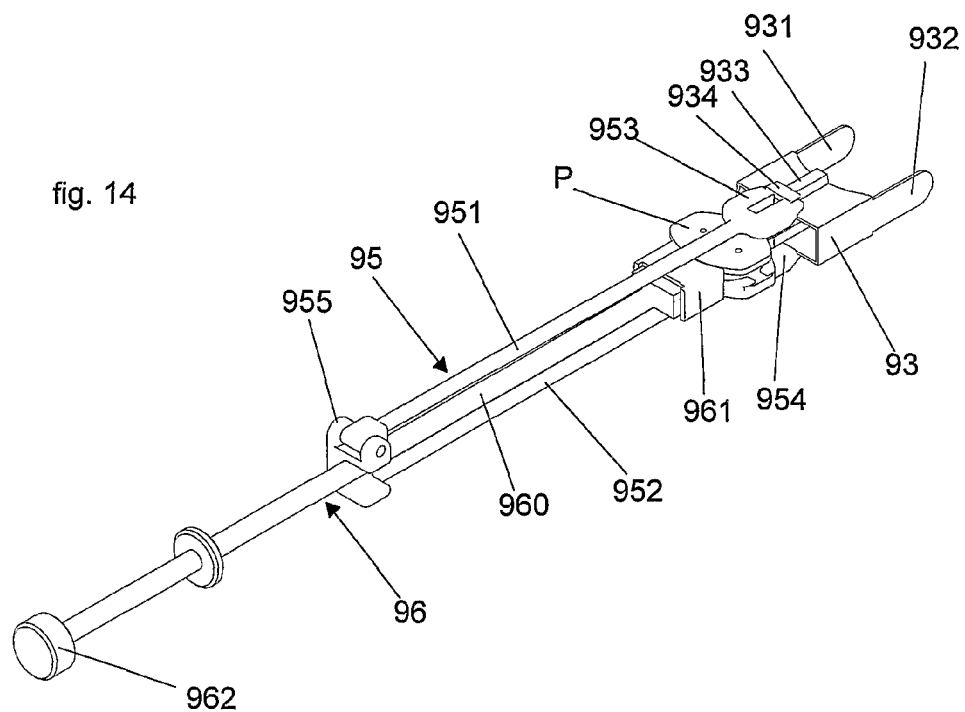
FIG. 14 represents a perspective view of the instrumentation according to an embodiment of the invention when the prosthesis is ready to be impacted in the disc space.

As well as illustrated in FIG. 14, these approach means (95) include two shafts (951, 952) connected to each other by articulation (955) so as to come to pinch the prosthesis (P) between two flattened parts ensuring a determined position of the prosthesis relative to these approach means. The ends of these shafts opposite the articulation including interlocking means (953, 954) capable of cooperating with the interlocking means (934, 936) of insertion guide (93) to ensure a determined position of approach means (95) relative to the insertion guide (93) as well as certain stability to this assembly. At the end of each shaft (951, 952), these interlocking means (953, 954) may in particular comprise a scalloping in which the arms come to encircle the exterior of the groove (933, 935) of the insertion guide while gliding under the upper bar of the "T" formed by the tongue (934, 936) provided by this same insertion guide.

Once the insertion guide (93) fitted instead of the distraction tools and the approach means (95) interlocked to this guide, the prosthesis is therefore in a stable position relative to the spinal column, and may be inserted in the insertion guide then slide up to the disc space. This displacement is achievable here with the aid of impacting means, or impactor (96) comprising an impacting end capable of pressing on the assembled prosthesis, distributed on both plates and without touching the nucleus. This impactor includes a central elongated part (960) that can be inserted in guiding means as an opening in the shape of a "U" provided by approach means (95) at their articulated end (955). This impactor includes another end (962) called assembling or striking, that can act to apply a continuous pressure or repeated shocks, with the hand or by any known tool or apparatus. Such an action, applied on the assembling end (962) of the impactor in the axis (d9) of the channel (90) then will be reverberated by the end (961) on the prosthesis, so as to cause its entrance then sliding in the channel (90) of the insertion guide (93), then its insertion or impaction in the intervertebral space.

In all the prosthesis devices according to the invention described here, it is necessary to understand that the distinctions of "lower plate" (represented on the bottom of the figures and referenced 1) and "upper plate" (represented on the top of the figures and referenced 3) are above all conventional, the device being able to be used in a different position, even inverse of that consisting of placing the lower plate toward the bottom of the vertebral column.

Thus, the invention proposes an intervertebral disc prosthesis device comprising at least three pieces, which parts include a plate (1) called lower and a plate (3) called upper (3) producing around at least one intermediate part called nucleus (2) an articulation by support or sliding between loadbearing surfaces (12, 15, 21, 23, 32) of said pieces, one of these pieces including at least one protruding part or accident of shape cooperating with the shape of at least one other of said pieces to form an stop limiting the possibilities of movement of the nucleus, characterized in that this stop operation uses at least one stop external to the loadbearing surfaces comprising at least one part (161, 163) protruding from at least one plate (1), located outside the loadbearing surface (12, 15) of said plate and including a face directed towards the interior of the prosthesis, this face cooperating with a peripheral part (6) of the nucleus (21, 23) situated outside its loadbearing surfaces (21, 23) and in which the surface is directed towards the exterior of the nucleus, to limit displacements of the nucleus in translation or in rotation or both in a plane approximately transverse to the spinal column.

According to a particular aspect, the loadbearing surfaces (21, 21a, 23) of the nucleus (2) in contact with the lower plate (1) and upper plate (3) present axes of symmetry (d21, d23, respectively) forming between them a determined angle (a2) that is not zero, so that a pressure (F) exerted on the two plates (1, 3) along directions perpendicular to their external surfaces induces an incline (a3) of these plates with each other.

According to a particular aspect, this external stop limits the movements in rotation of the nucleus (2) relative to at least one plate (1) by contact between parts (6, 161, 163) supporting each other by stop surfaces, this support being done along a direction approximately parallel to the normal of each of these stop surfaces.

According to a particular aspect, the external stop includes a tongue (6) protruding form the nucleus (6) which cooperates with one of the plates (1) by confining this tongue (6) in a housing (162) delimited by pillars (161) protruding from the internal race of this same plate (1) or by a recess (66) separating this tongue into two arms encircling a pillar (163) protruding from the internal face of this same plate (1), the internal face of a plate being defined at that oriented on the side of the nucleus.

According to a particular aspect, the end of at least one pillar (161, 162, 163) presents a section greater than its base, this enlargement of the pillar cooperating with the shape of the external stop tongue (6) of the nucleus (2) to limit the raising of this same nucleus relative to the plate (1) providing this pillar.

In the same spirit, the invention also proposes an intervertebral disc prosthesis device comprising at least three pieces, including a plate (1) called lower and a plate (3) called upper (3) producing around at least one intermediate element called nucleus (2) an articulation by support or sliding between loadbearing surfaces (12, 15, 21, 23, 32) of said parts, one of these parts including at least one protruding part or accident of shape cooperating with the shape of at least one other of said pairs to form an stop limiting the possibilities of movement of the nucleus, characterized in that the loadbearing surfaces (21, 21a, 23) of the nucleus (2) in contact with the lower plate (1) and upper plate (3) present axes of symmetry (d21, d23, respectively) forming between them a determined angle (a2) that is not zero so that a pressure (F) exerted on the two plate (1, 3) along directions perpendicular to their external surfaces induces an incline (a3) of these plates with each other.

According to a particular aspect this device is characterized in that the operation of the stop uses at least one stop external to the loadbearing surfaces comprising at least one part (161, 163) protruding from at least one plate (1) located outside the loadbearing surface (12, 15) of said plate and including a face directed towards the interior of the prosthesis, this face cooperating with a peripheral part (6) of the nucleus located outside its loadbearing surfaces (21, 23) and in which the surface is directed towards the exterior of the nucleus, to limit the displacements of the nucleus in translation or in rotation or both in a plane approximately transverse to the spinal column.

According to a particular aspect, when the two plates have their external faces (10, 30) parallel to each other, their loadbearing surfaces (12, 12a, 32) cooperate with the loadbearing surfaces (21, 21a, 23) of the nucleus (2) present axes of symmetry (d12, d32) forming a determined angle (a4) between them so that a pressure (F) exerted on the two plates (1, 3) along directions perpendicular to their external faces induces an incline (a5) of these plates with each other.

According to a particular aspect, the loadbearing surfaces (12, 32) provided by the internal face of the lower plate (1) and the internal face of the upper plate (3) are each in complementary contact with a supporting surface (21, 23, respectively) of the nucleus (2), and each present a shape, convex and concave, respectively, or inversely, this nucleus itself presenting a perimeter (20) approximately cylindrical along the axis of symmetry of its contact faces (21, 32).

According to a particular aspect, the internal face of the lower plate (1) presents a loadbearing surface (12a) cooperating with a loadbearing surface (21a) of the lower face of the nucleus (2), this same nucleus including on its upper face a convex loadbearing surface (23) in complementary contact with a concave loadbearing surface (32) of the internal face of the upper plate (3) the loadbearing surface (12a) of the internal face of the lower plate being sufficiently extended to allow movement of the nucleus relative to this same lower plate.

According to a particular aspect, an intermediate element called block (5) is added on the internal face of one (1) of the plates and produces an articulation with the other plate (3) around the nucleus (2) which nucleus presents a concave loadbearing surface (21) and a convex loadbearing surface (23) these two loadbearing surfaces being in contact in a complementary way with one loadbearing surface (52) of the block (5) one, and with a loadbearing surface (32) of the internal face of the plate (3) not including block, for the other.

According to a particular aspect, the axis of symmetry (d52) of the convex loadbearing surface (52) of the block (5) forms a determined angle (a4) with an axis (d51) perpendicular to its surface (51) with contact of the plate (1) so that a pressure (F) exerted on the two plates (1, 3) along directions perpendicular to their external faces induces an incline (a5) of the plates with each other.

According to a particular aspect, at least one of the loadbearing surfaces (12, 52, 21, 23, 32) allowing articulation has a shape making up part of a sphere.

According to a particular aspect, the loadbearing surfaces of the two faces of the nucleus (2) have shapes making up parts of a sphere, the face presenting a concave loadbearing surface (21) having a radius greater than that of the face presenting a convex loadbearing surface (23).

According to a particular aspect, each of the plates (1, 3) includes on its external face one or more protruding parts with small section forming a bony anchoring, these protruding parts coming to be embedded or impacted in the surface of contiguous bony elements (V) under the effect of pressure, once the prosthesis is in position between two vertebrae or bony elements.

According to a particular aspect, one or more of the pieces of the prosthesis include accidents of shape, notches (7) or perforations likely to see a tool again to facilitate the extraction of said prosthesis.

According to a particular aspect, the plates (1, 3) are composed of an alloy with base of stainless steel with cobalt-chromium and the nucleus (2) has polyethylene base.

In the same spirit, the invention proposes instrumentation for inserting or fitting the prosthesis according to one of claims 1 to 15 characterized in that it comprises an insertion guide (9,93) including an internal channel (90) presenting an end in which certain edges or support edges (910, 920, 931, 932), protrude from the others along the longitudinal axis (d9) of the channel so as to be able to take the place of distraction tools of a known type previously used to increase the opening of the disc space, this channel (90) presenting an internal section capable of surrounding these same distraction tools while they maintain this opening, then allowing their extraction through said channel while said support edges (910, 920, 931, 932), for their part, preserve the opening of the disc space by replacing the distraction tools, then receiving and guiding the prosthesis (P) for insertion in this disc space.

According to a particular aspect, the internal channel (90) presents an approximately rectangular section or with a shape approximately complementary to the exterior profile of the prosthesis, taken in a section along the plane perpendicular to the direction of insertion.

According to a particular aspect, the support edges (931, 932) of insertion guide (93) form an extension of the channel (90) walls located on a plane containing the axis of the spinal column.

According to a particular aspect, the insertion guide (9) is formed from at least two elements (91, 92) separated along one or more planes parallel to the longitudinal axis (d9) of the channel, these parts each including at least one portion of the transverse section of the channel and being able to be spread apart according to a determined angle (a9) and allowing the introduction and sliding of the prosthesis (P) in the channel.

According to a particular aspect, the internal surface of the channel (90) on its walls opposite external faces of the plates (1, 3) of the prosthesis (P), includes at least one groove (913, 914) allowing the passage of protruding parts (8, 81) for anchoring provided by these plates during displacement of the prosthesis in this channel (90).

According to a particular aspect, the instrumentation comprises approach means (95) of the prosthesis capable of receiving the prosthesis and of maintaining with it all the different components, these approach means (95) being able to be connected by interlocking means to the insertion guide (93) so as to present the prosthesis at the entrance of the channel (90) in a position appropriate for allowing its entrance into this channel (90).

According to a particular aspect, the instruments comprises insertion means, called impactor (96) of the prosthesis in the channel (90) of the insertion guide (93) then into the disc space, this impactor being guided by the support means (95) so as to be in contact with the prosthesis in its part opposite the entrance of the channel (90), this impactor (96) being able to apply or transmit a pressure or repeated shocks to the prosthesis to cause its sliding in the channel, then its insertion in the disc space.

According to a particular aspect, the support means include two shafts (951, 952) connected by an axis to a assembling end (955), these shafts being able to be closed up to pinch the prosthesis (P) between them and to maintain it so assembled, these two shafts each providing connection means to the guide for use (93), this connection then maintaining these two shafts closed up on the prosthesis.

It must be obvious for those skilled in the art that the present invention allows embodiments in numerous other specific forms without going far from the field of application of the invention as claimed. As a result, the present embodiments must be considered by way of illustration, but may be modified in the field defined by the scope of the attached claims, and the invention must not be limited to details given above.

The invention claimed is:

1. Instrumentation for surgically inserting an intervertebral prosthesis in a gap between a first vertebra and a second vertebra, the instrumentation comprising an insertion guide having a longitudinal axis and comprising:
   a first end having an opening through which the intervertebral prosthesis may pass and through which a distraction tool may be received;
   a second end having an opening through which the intervertebral prosthesis may pass and through which a distraction tool may be received;
   a channel extending from the first end to the second end arranged and configured with a passage permitting transit of the intervertebral prosthesis and the distraction tool along the longitudinal axis through the first end and through the second end, the channel comprising
      a first wall having an exterior surface orientable toward the first vertebra, a second wall disposed on an opposite side of the insertion guide from the first wall and having an exterior surface orientable toward the second vertebra, first and second opposing side walls each extending from the first wall to the second wall, a groove in the first wall or the second wall, the groove extending along the entire length of the passage and opening at the first and second ends, the groove being configured and arranged for passage of an anchor projecting from a surface of the intervertebral prosthesis completely through the guide, and edges protruding from at least one of the opposing side walls at the second end along the longitudinal axis, the edges configured and arranged to maintain separation of the first and second vertebrae during insertion of the intervertebral prosthesis.

2. Instrumentation of claim 1 in which the channel has an approximately rectangular cross section that is approximately complementary to the exterior profile of the prosthesis.

3. Instrumentation of claim 1 in which the edges are formed by extensions of walls of the channel.

4. Instrumentation of claim 1 further comprising plural elements forming the channel, which elements are adjustable to form a determined angle.

5. Instrumentation of claim 1 in which each of plural surfaces of the channel comprises a groove extending along a length of the channel through the openings of the first and second ends configured and arranged for passage of an anchor of the intervertebral prosthesis through the guide.

6. Instrumentation of claim 1 further comprising a support configured to hold the intervertebral prosthesis stable during approach to the channel.

7. Instrumentation of claim 6 further comprising an impactor cooperating with a guide of the support, the impactor having a striking end configured for application of a force and an impacting end configured to transmit the force to the intervertebral prosthesis.

8. Instrumentation for surgically inserting an intervertebral prosthesis in a gap between the opposing endplates of two adjacent vertebrae comprising an insertion guide comprising:
a longitudinal axis,
a first end and a second end each having an opening through which the intervertebral prosthesis may pass and through which a distraction tool may extend,
a channel extending from the first end to the second end and having a generally rectangular cross section with opposing generally planar walls configured for alignment with the opposing endplates, the channel arranged and configured for passage along the longitudinal axis of the intervertebral prosthesis and the distraction tool through the first end and the second end, with at least one of the opposing generally planar walls comprising a scallop extending along a length of the channel and configured and arranged for passage of an anchor projecting from a surface of the intervertebral prosthesis through the guide and into one of the vertebrae, and
vertebral support walls of the channel configured to support the adjacent vertebrae during insertion of the intervertebral prosthesis; and
an assembly tool having at least one interlock configured for engagement with a cooperating interlock of the insertion guide, with the interlock of the assembly tool comprising a hook and the interlock of the insertion guide comprising a tongue.

9. Instrumentation for surgically inserting an intervertebral prosthesis in a gap between the opposing endplates of two adjacent vertebrae comprising an insertion guide comprising:
a longitudinal axis,
a first end and a second end each having an opening through which the intervertebral prosthesis may pass and through which a distraction tool may extend,
a channel extending from the first end to the second end and having a generally rectangular cross section with opposing generally planar walls configured for alignment with the opposing endplates, the channel arranged and configured for passage along the longitudinal axis of the intervertebral prosthesis and the distraction tool through the first end and the second end, with at least one of the opposing generally planar walls comprising a scallop extending along a length of the channel and configured and arranged for passage of an anchor projecting from a surface of the intervertebral prosthesis through the guide and into one of the vertebrae, and
vertebral support walls of the channel configured to support the adjacent vertebrae during insertion of the intervertebral prosthesis; and
a support configured to position and support the intervertebral prosthesis during its approach to the gap comprising shafts connected by an articulation.

10. Instrumentation for surgically inserting an intervertebral prosthesis in a gap between the opposing endplates of two adjacent vertebrae comprising an insertion guide comprising:
a longitudinal axis,
a first end and a second end each having an opening through which the intervertebral prosthesis may pass and through which a distraction tool may extend,
a channel extending from the first end to the second end and having a generally rectangular cross section with opposing generally planar walls configured for alignment with the opposing endplates, the channel arranged and configured for passage along the longitudinal axis of the intervertebral prosthesis and the distraction tool through the first end and the second end, with at least one of the opposing generally planar walls comprising a scallop extending along a length of the channel and configured and arranged for passage of an anchor projecting from a surface of the intervertebral prosthesis through the guide and into one of the vertebrae, and
vertebral support walls of the channel configured to support the adjacent vertebrae during insertion of the intervertebral prosthesis; and
a support configured to position and support the intervertebral prosthesis during its approach to the gap comprising an interlock configured to engage a complementary interlock of the insertion guide.

11. Instrumentation of claim 10 in which the interlock of the support comprises a scallop and the interlock of the insertion guide comprises a tongue.

* * * * *